United States Patent
Collu et al.

(10) Patent No.: US 12,351,782 B2
(45) Date of Patent: *Jul. 8, 2025

(54) LIQUID TREATMENT COMPOSITIONS COMPRISING DELIVERY PARTICLES BASED ON PLANT ROSIN MATERIAL

(71) Applicant: The Procter & Gamble Company, Cincinnati, OH (US)

(72) Inventors: Mattia Collu, Saint-Gilles (BE); Cédric Marc Tahon, Oost-Vlaanderen (BE); Johan Smets, Lubbeek (BE)

(73) Assignee: The Procter & Gamble Company, Cincinnati, OH (US)

( * ) Notice: Subject to any disclaimer, the term of this patent is extended or adjusted under 35 U.S.C. 154(b) by 628 days.

This patent is subject to a terminal disclaimer.

(21) Appl. No.: 17/549,916

(22) Filed: Dec. 14, 2021

(65) Prior Publication Data

US 2022/0186147 A1 Jun. 16, 2022

Related U.S. Application Data

(60) Provisional application No. 63/125,986, filed on Dec. 16, 2020.

(51) Int. Cl.
| | | |
|---|---|---|
| *C11D 1/00* | (2006.01) | |
| *C11D 3/00* | (2006.01) | |
| *C11D 3/38* | (2006.01) | |
| *C11D 3/382* | (2006.01) | |
| *C11D 3/50* | (2006.01) | |

(52) U.S. Cl.
CPC .......... *C11D 3/382* (2013.01); *C11D 3/0015* (2013.01); *C11D 3/505* (2013.01)

(58) Field of Classification Search
CPC .......... C11D 1/00; C11D 3/0015; C11D 3/38; C11D 3/382; C11D 3/50; C11D 3/505

See application file for complete search history.

(56) References Cited

U.S. PATENT DOCUMENTS

| | | | |
|---|---|---|---|
| 2,571,689 A | 10/1951 | Maria et al. | |
| 2,776,276 A | 1/1957 | Glasebrook et al. | |
| 3,950,510 A | * 4/1976 | Adams ................. | A61K 8/922 |
| | | | 510/432 |
| 5,362,715 A | 11/1994 | Cohen | |
| 5,478,567 A | 12/1995 | Nakagawa et al. | |
| 6,869,923 B1 | 3/2005 | Cunningham | |
| 7,438,897 B2 | 10/2008 | Gupta | |

(Continued)

FOREIGN PATENT DOCUMENTS

| | | |
|---|---|---|
| EP | 0138597 A2 | 4/1985 |
| EP | 1038910 A1 | 9/2000 |

(Continued)

OTHER PUBLICATIONS

All Office Actions; U.S. Appl. No. 17/549,922, filed Dec. 14, 2021.

(Continued)

*Primary Examiner* — Brian P Mruk
(74) *Attorney, Agent, or Firm* — Carolyn S. Powell

(57) ABSTRACT

Liquid treatment composition that include particles and an adjunct ingredient, where the particles include a plant rosin material and one or more benefit agents. Related methods of making and using such compositions.

18 Claims, 3 Drawing Sheets

(56) References Cited

U.S. PATENT DOCUMENTS

| | | |
|---|---|---|
| 7,795,476 B2 | 9/2010 | Corzani |
| 8,802,729 B2 | 8/2014 | Fenyvesi et al. |
| 9,186,642 B2 | 11/2015 | Dihora |
| 10,582,705 B2 | 3/2020 | Conover |
| 2002/0018760 A1 | 2/2002 | Vatter et al. |
| 2004/0121926 A1 | 6/2004 | Waits et al. |
| 2006/0020057 A1 | 1/2006 | Maas et al. |
| 2006/0154850 A1 | 7/2006 | Quellet |
| 2007/0129476 A1 | 6/2007 | Macbeath et al. |
| 2010/0089420 A1 | 4/2010 | Greenberg |
| 2013/0125297 A1 | 5/2013 | Pagani |
| 2019/0153354 A1 | 5/2019 | Lankin et al. |
| 2019/0373883 A1* | 12/2019 | Conover ............ A01N 25/34 |

FOREIGN PATENT DOCUMENTS

| | | |
|---|---|---|
| EP | 2746379 A1 | 6/2014 |
| GB | 1340043 A | 12/1973 |
| GB | 1349741 A | 4/1974 |
| GB | 1419116 A | 12/1975 |
| GB | 1515299 A | 6/1978 |
| IT | 202000004684 A1 | 9/2021 |
| JP | 2001262199 A | 9/2001 |
| WO | 2011030158 A2 | 3/2011 |
| WO | 2019051165 A1 | 3/2019 |
| WO | 2020058373 A1 | 3/2020 |
| WO | 2020234263 A1 | 11/2020 |

OTHER PUBLICATIONS

All Office Actions; U.S. Appl. No. 17/549,919, filed Dec. 14, 2021.
All Office Actions; U.S. Appl. No. 17/549,923, filed Dec. 14, 2021.
Glycerol ester of wood rosin INV, XP55811290 Retrieved from the Internet URL:https://en.wikipedia.org/wiki/Glycerolester of wood rosin, dated Mar. 4, 2021, p. 2.
Database GNPD Mintel,"Moist Diane Extra Moist & Shine Hair Mask has been relaunched", http:llwww.gnpd.comT, dated Jan. 29, 2020 pp. 3.
Eastman rosin products, "Natural resins for adhesion, wetting, viscocity control", pp. 08.
Mahmoud Abdul-Raheim,"BAOJ Chemistry Rosin Chemistry, Derivatives, and Applications a review", vol. 4, dated 2018, p. 2 of 16.
Polymer Properties Database, "Rosin Esters and Polymers", https://polymerdatabase.com/polymer classes/Rosin.html, dated 2015, pp. 03.
Satish Kumar Gupta,"Rosin: A naturally derived excipient in drug delivery systems, Department of Pharmaceutical Technology", dated 2013, pp. 05.
Unpublished U.S. Appl. No. 17/549,919, filed Dec. 14, 2021, to first inventor Mattia Collu et. al.
Unpublished U.S. Appl. No. 17/549,922, filed Dec. 14, 2021, to first inventor Mattia Collu et. al.
Unpublished U.S. Appl. No. 17/549,923, filed Dec. 14, 2021, to first inventor Mattia Collu et. al.
15937 PCT Search Report and Written Opinion for PCT/US2021/072888 dated Apr. 21, 2022, 13 pages.
Bambang Wiyono et al. "Chemical Compositions of Pine Resin, Rosin and Turpentine Oil from West Java", Journal of Forestry Research, vol. 3, No. 1, dated Mar. 1, 2016; pp. 7-17.
Database GNPD Mintel; "Foundation EX SPF 50+ PA++++", http://www.gnpd.com, dated May 2020; 5 Pages.
Database GNPD Mintel; "Hair Color Treatment", http://www.gnpd.com, dated Nov. 17, 2016; 4 Pages.
Database GNPD Mintel; "Light Luminous Hydrating Lipstik" http://www.gnpd.com; dated Jul. 1, 2020; 4 Pages.
Database GNPD Mintel; "Moisturizing Lip Balm", http;//www.gnpd.com, dated Nov. 10, 2020 , 3 Pages.
Database GNPD Mintel; "Shaving Oil", http://www.gnpd.com, dated May 2, 2018 , 5 Pages.

* cited by examiner

LIQUID TREATMENT COMPOSITIONS COMPRISING DELIVERY PARTICLES BASED ON PLANT ROSIN MATERIAL

This application claims benefit to Provisoinal Ser. No. 63/125,986, filed on Dec. 16, 2020.

FIELD OF THE INVENTION

The present disclosure relates to liquid treatment compositions that include particles and an adjunct ingredient, where the particles include a plant rosin material and one or more benefit agents. The present disclosure also relates to related methods of making and using such compositions.

BACKGROUND OF THE INVENTION

Treatment compositions, such as liquid fabric softeners, can employ various delivery systems to facilitate improved delivery of benefit agents. Particles are commonly selected as a delivery system, particularly for perfumes.

For example, perfume may be encapsulated in a core-shell particle to enable improved perfume deposition and freshness benefits across multiple touchpoints. Other materials, such as amphiphilic graft co-polymers, are disclosed as being able to associate with benefit agents to form particles that can subsequently deposit onto a surface, such as a fabric.

However, one drawback of these delivery systems is that they typically require synthetic materials, such as synthetic polymers, whereas manufacturers, vendors, and consumers have an increased desire to use materials that are derived from natural and/or sustainable sources.

Additionally or alternatively, some of the materials used to encapsulate or entrap benefit agents are susceptible to dilution, resulting in release of the benefit agent during an aqueous treatment cycle. Because the release occurs prior to deposition on the target surface, the performance of the benefit agent is dampened at certain touch points, such as on dried fabrics.

There is a continued need for treatment compositions that offer improved benefit-agent-delivery mechanisms that are derived from natural sources.

SUMMARY OF THE INVENTION

The present disclosure relates to liquid treatment compositions that include particles and an adjunct ingredient, where the particles comprise a plant rosin material and one or more benefit agents.

The present disclosure also relates to a liquid treatment composition that includes particles and an adjunct ingredient, where the particles include a tricyclic diterpene monocarboxylic acid, a derivative thereof, or a mixture thereof, where the particles further include one or more benefit agents, preferably where the tricyclic diterpene monocarboxylic acid, the derivative thereof, or the mixture thereof includes a material selected from abietic-type acids, derivatives thereof, pimaric-type acids, derivatives thereof, and mixtures thereof, more preferably where the tricyclic diterpene monocarboxylic acid includes a derivative in the form of an ester.

The present disclosure also relates to a method of treating a surface, preferably a fabric, where the method includes the step of contacting the surface with the liquid treatment composition as described herein, optionally in the presence of water.

BRIEF DESCRIPTION OF THE DRAWINGS

The figures herein are illustrative in nature and are not intended to be limiting.

DETAILED DESCRIPTION OF THE INVENTION

Figure 1:
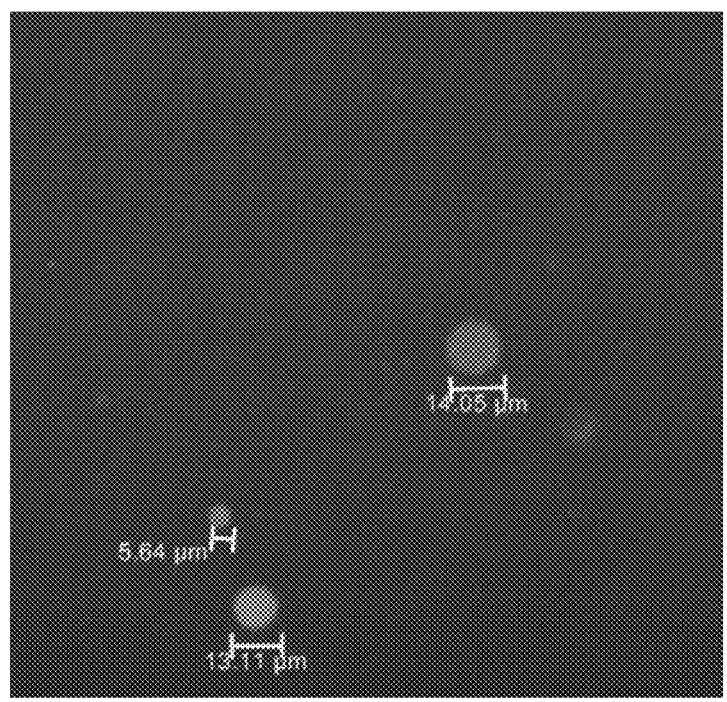
FIG. 1 shows a liquid treatment composition comprising particles, as described in Example 2 below.

The present disclosure relates to liquid treatment composition that comprise benefit-agent-delivery particles (or just "particles," as used herein). The particles of the present disclosure comprise a plant rosin material and one or more benefit agents, such as perfume. As indicated in the name, plant rosin materials are derived from plants, typically from pine trees, and therefore are attractive as natural or sustainable materials, even if subsequently modified or derivatized.

It has surprisingly been found that particles comprising the plant rosin materials of the present disclosure and benefit agents can act as effective delivery systems in liquid treatment compositions. These rosins typically are characterized by high levels of, for example, abietic acid. Without being bound by theory, it is believed that the structure of the abietic-acid-type materials structure leads to interactions w/perfume raw materials resulting from hydrophobic regions. This can lead to the formation of relatively large particles that are relatively stable. It is believed that the particles can withstand water dilution; for instance in the case of a fabric care product, they are resistant to the dilution step in the washing cycle and therefore maintain an association that facilitates benefit agent deposition. Furthermore, it is believed that the rosin material is characterized by a relatively high molecular weight, which makes it more likely to deposit on target surfaces, such as fabrics, compared to other, smaller compounds.

The components, compositions, and processes of the present disclosure are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Treatment Composition

The present disclosure relates to liquid treatment compositions that comprise particles and an adjunct ingredient.

The treatment composition may be a consumer product composition. The consumer product composition may be a fabric care composition, a hard surface cleaner composition, a dish care composition, a hair care composition, a body cleansing composition, or a mixture thereof. The consumer product composition may be a conditioning composition, such as a liquid fabric enhancer composition or a hair conditioner composition.

The treatment compositions of the present disclosure may be fabric care compositions. Such compositions may be used as a pre-laundering treatment, a post-laundering treatment, or may be added during the rinse or wash cycle of the laundering operation. The fabric care composition may be a fabric detergent composition, a fabric conditioning composition, or a mixture thereof, preferably a fabric conditioning composition. Fabric conditioning compositions may include liquid fabric softeners and liquid fabric enhancing compositions.

The treatment composition may be encapsulated in a water-soluble film, so as to be in the form of a unitized unit dose article, such as a pouch. The water-soluble film may be a polyvinyl alcohol water-soluble film. Suitable films are available from MonoSol, LLC (Indiana, USA). The treatment composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof: in such cases, at least one encapsulated composition is a liquid composition. Unit dose articles such as pouches, as well as water-soluble films, are described in more detail below.

The composition may be characterized by a viscosity. The composition may have a viscosity of from about 1 to about 1500 centipoises (about 1-1500 mPa*s), from about 50 to about 1000 centipoises (about 50-1000 mPa*s), or from about 100 to 500 centipoises (about 100-500 mPa*s), or from about 100 to about 200 centipoises (about 100-200 mPa*s), at 20 $s^{-1}$ and 21° C., is disclosed. Relatively lower viscosities allow for improved dosing and/or less residue in a dispenser drawer. Viscosity is determined according to the method provided in the Test Methods section below.

The treatment compositions of the present disclosure may be characterized by a pH of from about 2 to about 12, or from about 2 to about 8.5, or from about 2 to about 7, or from about 2 to about 5. The treatment compositions of the present disclosure may have a pH of from about 2 to about 4, preferably a pH of from about 2 to about 3.7, more preferably a pH from about 2 to about 3.5, preferably in the form of an aqueous liquid. It is believed that such pH levels facilitate stability of certain adjuncts, such as conditioning actives (e.g., esterquats). The pH of a composition is determined by dissolving/dispersing the composition in deionized water to form a solution at 10% concentration, at about 20° C.

Delivery Particles (or "Particles")

The present disclosure relates to delivery particles, also simply called "particles" in the present disclosure. The particles comprise a plant rosin material and one or more benefit agents.

The one or more benefit agents may be encapsulated in the plant rosin material, and/or embedded in the plant rosin material. Compositions of the present disclosure may comprise the presently described particles.

The particles of the present disclosure may be present in a population, which may have a volume-weighted average diameter (or "diameter" as used herein). Volume-weighted average diameter is determined according to the method provided in the Test Method section below. The particles may have a volume-weighted average diameter of from about 10 microns to about 400 microns. Without being bound by theory, it is believed that particles that are smaller will not be as effective as a delivery particle, and particles that are larger may be visible in the final product and/or cause undesirable spotting on a target surface. Particles on the lower end of the range may be preferred to increase the efficiency of perfume delivery, as larger particles tend to include a relatively higher ratio of rosin material to perfume. The particles may be characterized by a volume-weighted median particle size of from about 10 microns to about 400 microns, or from about 15 microns to about 300 microns, or from about 20 microns to about 250 microns, or from about 25 microns to about 200 microns, or from about 30 microns to about 150 microns, or from about 35 to about 125 microns, preferably from about 40 to about 100 microns, more preferably from about 50 to about 90 microns.

One or more particles of the present disclosure may comprise at least one region comprising a benefit agent, such as a perfume raw material or enzyme. The region may comprise a benefit agent, such as a perfume raw material or enzyme, being encompassed or encapsulated within the plant rosin material. The region may comprise a benefit agent, such as a perfume raw material or enzyme, being embedded, for example partially embedded, within the plant rosin material.

One or more particles of the present disclosure may have a structure selected from the group consisting of (a) a particle comprising a single region having benefit agent that is embedded in the plant rosin material; (b) a particle comprising at least two regions having benefit agents that are embedded in the plant rosin material; (c) a particle comprising at least one region having benefit agents that is at least partially embedded on the surface of the plant rosin material; (d) a particle comprising a single region having a benefit agent that is embedded in the plant rosin material and at least one region having a benefit agent that is at least partially embedded on the surface of the plant rosin material; and (e) a particle comprising at least two regions having benefit agents that are embedded in the plant rosin material and at least one region having a benefit agent that is at least partially embedded on the surface of the plant rosin material. Compositions of the present disclosure may include one or more particles having a structure according to (a)-(e), or mixtures thereof.

The particles may be characterized by a weight ratio of the plant rosin material to the benefit agent (e.g., preferably perfume). The plant rosin material and the one or more benefit agents may be present in the particles in a weight ratio of from about 5:95 to about 95:5, preferably from about 20:80 to about 80:20, more preferably from about 30:70 to about 70:30, more preferably from about 40:60 to about 60:40. The weight ratio may be from about 50:50 to about 80:20, or from about 50:50 to about 70:30. Rosin material: benefit agent weight ratios closer to 50:50 may be preferred to give a relatively good balance of performance and processing ease; ratios relatively higher than 50:50 may provide for improved performance, provided the benefit agent is added/present at a consistent level.

The treatment compositions of the present disclosure may comprise from about 0.01% to about 10%, or from about 0.05% to about 7%, or from about 0.1% to about 5%, more preferably from 0.8% to 4%, or from about 1% to about 3%, by weight of the treatment composition, of the rosin-based particles. Such particles may comprise rosin material and a benefit agent (preferably, perfume raw materials) in a weight ratio of 70:30 to 50:50.

The plant rosin material and the benefit agents of the particles are described in more detail below.

a. Plant Rosin Material

The compositions, particles, and processes described herein contain plant rosin material. As used herein, "plant rosin material" may include plant rosins (including resin acids), plant rosin derivatives, or mixtures thereof. Plant rosin material in the present compositions, particles, and processes can provide performance benefits, for example by facilitating improved deposition and/or stability of benefit agents. Such materials may further be preferred to known alternatives in the presently disclosed compositions and processes because they are derived from natural and/or sustainable resources.

As discussed in more detail below, plant rosin is typically derived from conifer plants (class: Pinopsida), usually from pine trees (genus: *Pinus*). Also called "colophony," plant rosin is a solid material produced by heating liquid resins to vaporize the volatile liquid terpene components. Plant rosins are typically composed of resin acids such as abietic acid and related compounds. Plant rosins may be further derivatized, for example through esterification and/or hydrogenation.

The compositions of the present disclosure may comprise from about 0.01% to about 10%, by weight of the composition, of plant rosin material. The compositions may comprise from about 0.01% to about 5%, or from about 0.05% to about 3%, or from about 0.1% to about 1%, by weight of the composition of plant rosin material.

Plant rosin materials may be characterized by a softening point. Plant rosin materials are typically solid at room temperature, but the softening point is a measure of the glass transition temperature associated with these materials. The softening point of a plant rosin material is determined according to method provided in the Test Method section below.

The plant rosin material may be characterized by a softening point of from about 50° C. to about 175° C., or from about 60° C. to about 150° C., or from about 75° C. to about 125° C. Rosins may need to be softened by heating in order to be incorporated into consumer products. Thus, for ease of processing and/or energy savings, plant rosin materials having relatively lower softening points (e.g., less than 125° C.) may be preferred for the compositions and processes of the present disclosure. Lower softening points may also have an effect on improving the deposition aid performance of the plant rosin material.

Plant rosin materials may be characterized by an acid number (sometimes called "acid value"). The acid number of a plant rosin material relates to the total free acid content of these products. The acid number of a plant rosin material is determined according to method provided in the Test Method section below.

Plant rosin materials may be characterized by an acid number less than about 175, e.g., from about 0 to about 175. For the particles, compositions, and processes of the present disclosure, it may be preferred to use plant rosin material having a relatively low acid number, such as less than about 125, preferably less than about 100, more preferably less than about 75, even more preferably less than about 50, more preferably less than about 25, so as to have minimal effect on the final pH of the treatment composition. Without being bound by theory, it is believed that plant rosin materials having a relatively low acid number may also be more easily dispersible in the treatment compositions of the present disclosure.

The color of the plant rosin material may be graded based on the Gardner Color standard number, ranging 1 to 18. So as to have minimal effect on the final color of the treatment composition, preferred plant rosin materials of the present disclosure may have a color grade of from about 1 to about 10, preferably from about 1 to about 8. The color grade of a plant rosin material is determined according to method provided in the Test Method section below.

Plant rosin materials may have an odor. Naturally derived resins have an abundance of terpenic compounds. For the compositions and processes of the present disclosure, it may be preferred to select compound with a relatively low amount of terpenic structures and/or odor, so that the naturally derived resin will not interfere with the overall character perception. On the other hand, if there is a desire for a pine-tree-like fragrance character, then the presence of terpenic structures may be preferred.

For example, gum rosins may be preferred over tall oil rosins, as tall oil rosins may include sulfur contaminants that affect the odor. On the other hand, it may be desirable for the plant rosin materials to have a detectable odor, as the "piney" scent associated with rosin material may be useful or desirable in a particular product composition.

Plant rosin materials are typically relatively insoluble in water. For example, plant resin materials according to the present disclosure may be characterized by a solubility of less than 1 g/L, or less than 100 g/L, or less than 1 g/L, or less than 0.1 g/L, or less than about 0.01 g/L, in deionized water at 22° C. Without wishing to be bound by theory, it is believed that the relatively insoluble nature of the plant rosin materials of the present disclosure contribute to the deposition efficiency and performance of the associated benefit agent. For example, it is believed that compared to particles comprising PEG/vinyl acetate graft co-polymers, the rosin-based particles of the present disclosure are less likely to dissolve or dissemble when the treatment composition is diluted during a treatment process, such as the wash or rinse cycle of an automatic washing machine, resulting in improved deposition and performance.

Plant rosin materials may be characterized by a density. Typically, the plant rosin materials are characterized by a density of at greater than 1.0 kg/dm$^3$, preferably at least 1.1 kg/dm$^3$, at 25° C.

Plant rosin materials are typically flammable. For the particles, compositions, and processes of the present disclosure, it may be preferred to use plant rosin materials that have a relatively high flash point, e.g., higher than 190° C., to facilitate easier and safer processing. The flash point of a plant rosin material is determined according to method provided in the Test Method section below.

The treatment compositions of the present disclosure may comprise particles that comprise plant rosin material, where the plant rosin material may comprise a material selected from the group consisting of gum rosin, wood rosin, tall oil rosin, derivatives thereof, and mixtures thereof; preferably gum rosin, derivatives thereof, and mixtures thereof, more preferably a gum rosin ester. The plant rosin material may be a plant rosin ester, preferably an ester formed from an alcohol having two or more carbon atoms, more preferably where the alcohol is glycerol, pentaerythritol, or a mixture thereof. The plant rosin material may be at least partially hydrogenated, preferably fully hydrogenated. The plant rosin material may comprise at least 50%, more preferably at least 60%, more preferably at least 70%, more preferably at least 80%, more preferably at least 85%, by weight of the plant rosin material, of an abietic-type acid, a derivative of an abietic-type acid, or a mixture thereof.

Plant rosins and plant rosin derivatives, as well as pre-mixes comprising such substances, are discussed in more detail below.

1. Plant Rosins

The plant rosin material of the present disclosure may comprise a plant rosin. Plant rosin is typically obtainable from a plant's oleo-resin, which is may be exuded or otherwise derived from a pine tree. The oleo-resin may be distilled to remove volatile terpenes, and the solid material left behind is the plant rosin.

Plant rosin may be solid at room temperature. The solid rosin may be relatively translucent and/or glass-like. The plant rosin material may have a color ranging, for example from faint yellow to a darker brown color, or even black.

Plant rosin is typically a mixture of compounds and is primarily composed of resin acids (also called rosin acids). The plant rosin may comprise at least about 75%, or at least about 80%, or at least about 85%, or at least about 90%, or at least about 95%, by weight of the plant rosin, of resin acids. The plant rosin may comprise from about 75% to about 97%, or from about 80% to about 96%, or from about 85% to about 95%, or from about 90% to about 95%, by weight of the plant rosin, of resin acids. The remaining material may be non-acidic material.

Resin acids are typically monocarboxylic acids having three fused rings. Resin acids may be tricyclic diterpene monocarboxylic acids, for example with a molecular formula of $C_{19}H_{29}COOH$. Resin acids may include abietic-type acids, pimaric-type acids, plicatic acid, or mixtures thereof. The double bonds in abietic-type acids are typically conjugated, whereas the double bonds in pimaric-type acids are not typically conjugated.

Abietic-type acids may include abietic acid, neoabietic acid, dehydroabietic acid, palustric acid, levopimaric acid, or mixtures thereof. Pimaric-type acids may include pimaric acid, isopimaric acid, sandaracopimiaric acid, or mixtures thereof. Structures for these illustrative resin acids are provided below in Table A.

TABLE A

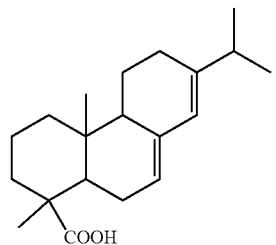 [SMILES: CC(C)C1=CC2=CCC3C(C)(C(=O)O)CCCC3(C)C2CC1]

Abietic acid

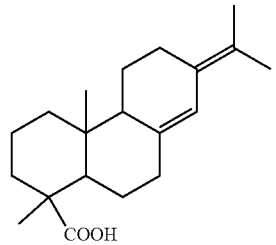 [SMILES: CC(C)=C1C=C2CCC3C(C)(C(=O)O)CCCC3(C)C2CC1]

Neoabietic acid

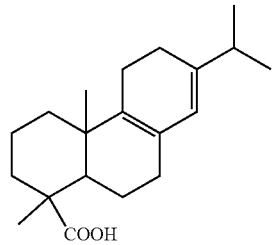 [SMILES: CC(C)C1=CC2=C(CC1)C1(C)CCCC(C)(C(=O)O)C1CC2]

Palustric acid

TABLE A-continued

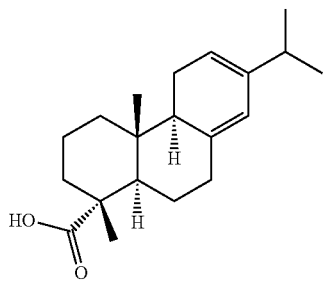

Levopimaric acid

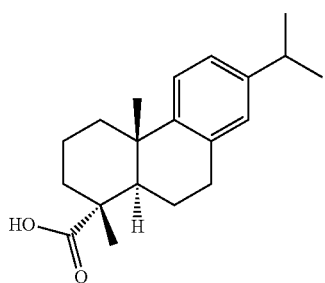 [SMILES: CC(C)c1ccc2c(c1)CC[C@H]1[C@](C)(C(=O)O)CCC[C@]21C]

Dehydroabietic acid

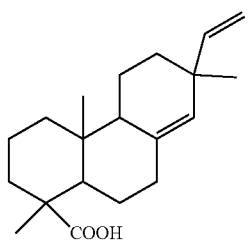 [SMILES: C=CC1(C)C=C2CCC3C(C)(C(=O)O)CCCC3(C)C2CC1]

Pimaric acid

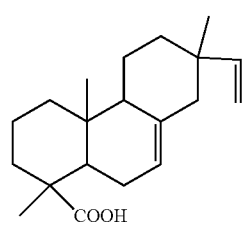 [SMILES: C=CC1(C)CCC2C(=CCC3C(C)(C(=O)O)CCCC23C)C1]

Isopimaric acid

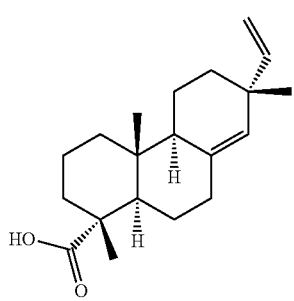

Sandaracopimiaric acid

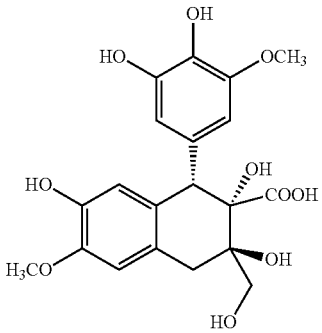 [SMILES: COc1cc2c(cc1O)[C@H](c1cc(O)c(O)c(OC)c1)[C@@](O)(C(=O)O)[C@](O)(CO)C2]

Plicatic acid

The plant rosin may comprise an abietic-type acid, preferably abietic acid. Abietic acid has the empirical formula $C_{19}H_{29}COOH$ and is also known as abietinic acid or sylvic acid. Abietic-type acids are typically the major component of a plant rosin. The plant rosin may comprise at least 5000, or at least 60%, or at least 70%, or at least 80%, or at least 85%, by weight of the plant rosin, of an abietic-type acid, preferably abietic acid.

Plant rosins may be classified depending on the source where it is obtained. For example, plant rosins of the present disclosure may be classified as (and may comprise) gum rosin, wood rosin, tall oil rosin, or a mixture thereof. Gum rosin may be derived from a resin extrudate of a tree or other plant and may be harvested by tapping or wounding the tree and then collecting and processing the extrudate. Wood rosin may be derived from materials that are harvested from pine tree stumps, for example through solvent extraction and/or distillation. Tall oil rosin is a by-product of the distillation of crude tall oil during the Kraft process of wood pulp manufacture when pulping pine trees.

Suitable plant rosins may be obtained, for example, from a variety of pine species, such as *Pinus massoniana* (Masson's pine), *P. elliotti* (slash pine), *P. palustris* (longleaf pine), *P. taeda* (loblolly pine), *P. oocarpa* (Mexican yellow pine), *P. leiophylla* (Chihuahua pine), *P. devoniana* (pino lacio, or Michoacan pine), *P. montezumae* (Montezuma pine), *P. pinaster* (maritime pine), *P. sylvestris* (Scots pine), *P. halepensis* (Aleppo pine), *P. insularis* (Benguet pine), *P. kesiya* (Khasi pine), *P. strobus* (Eastern white pine), or mixtures thereof.

2. Plant Rosin Derivatives

The plant rosin material of the present disclosure may comprise a plant rosin derivative. A plant rosin derivative may be made by chemically modifying a plant rosin material, such as a rosin acid such as abietic acid. Such derivatives may be produced by esterification, hydrogenation, dimerization, polymerization, saponification, or mixtures thereof. Thus, the plant rosin derivative may comprise a rosin ester, a hydrogenated rosin, a hydrogenated rosin ester, a dimerized rosin, a polymerized rosin, or mixtures thereof.

The plant rosin material may be a plant rosin ester. A plant rosin ester may be the reaction product of a plant rosin (e.g., a rosin acid) and an alcohol. A sample condensation reaction between three abietic acid molecules and one glycerol molecule is shown below, resulting in a rosin ester.

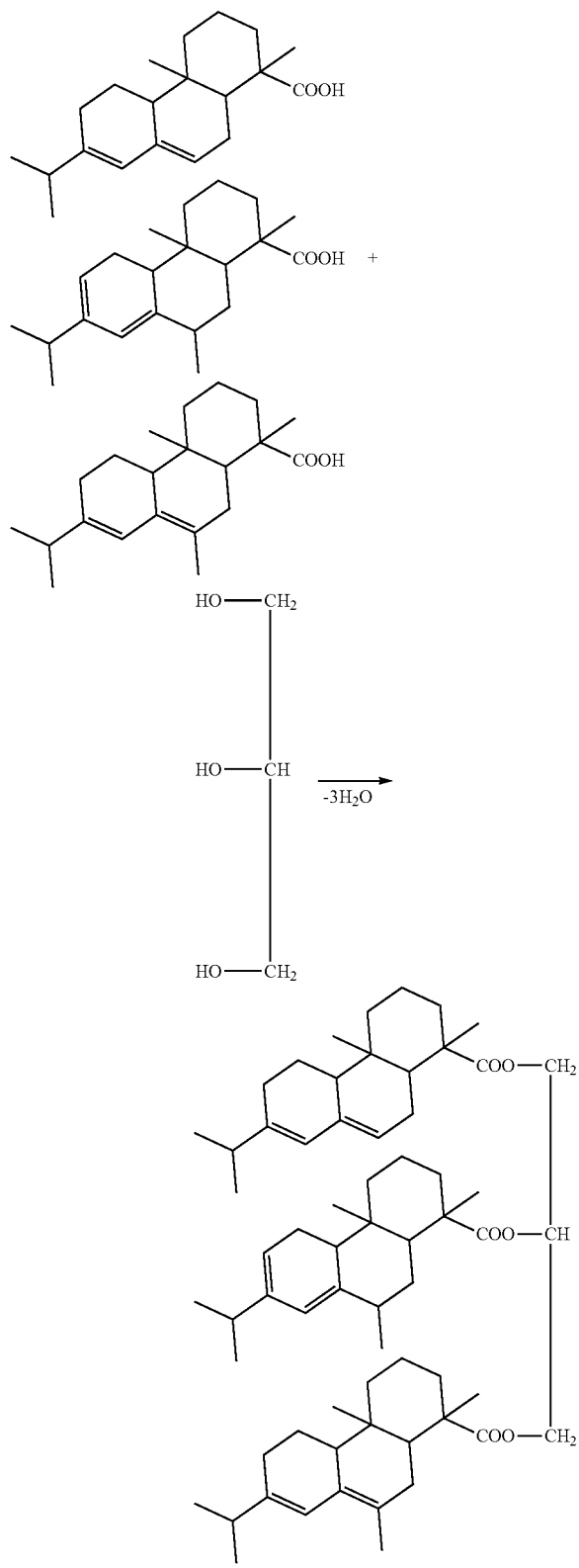

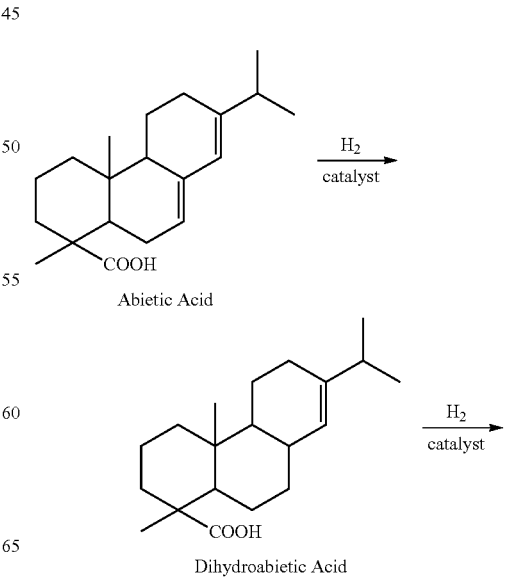

Abietic Acid

Dihydroabietic Acid ylene glycol. The alcohol may be a polyol that comprises three or more hydroxyl groups. Suitable polyols may include a total of three hydroxyl groups (e.g., glycerol), a total of four hydroxyl groups (e.g., pentaerythritol), or a total of six hydroxyl groups (e.g., sorbitol or mannitol). Preferred polyols include glycerol, pentaerythritol, and mixtures thereof.

The alcohol in the esterification reaction may comprise between 1 and 10 carbon atoms, preferably between 1 and 7, more preferably from between 1 and 6, even more preferably between 1 and 5, even more preferably between 3 and 5 carbon atoms. It may be preferred that the alcohol in the esterification reaction comprises at least 2 carbon atoms, preferably from 2 to 10, more preferably from 2 to 6, even more preferably from 2 to 5 carbon atoms. It may be preferred that the rosin ester is not a methyl ester.

The alcohol used in the esterification reaction may have a relatively low molecular weight. For example, the alcohol may have a molecular weight of from about to about 32 daltons to about 300 daltons, preferably from about 32 daltons to about 200 daltons, more preferably from about 32 daltons to about 150 daltons, even more preferably from about 90 daltons to about 150 daltons. Without wishing to be bound by theory, it is believed that a rosin ester formed from a lower-molecular-weight alcohol is likely to be characterized by a relatively lower softening point and/or a lower acid value compared to a rosin ester formed from a relatively higher-molecular-weight alcohol, thereby leading to better processability and/or performance.

The alcohol used in the esterification reaction may be glycerol or pentaerythritol. Thus, the plant rosin derivative may be a glyceryl rosin ester, a pentaerythrityl rosin ester, or a mixture thereof.

The plant rosin derivative may be a hydrogenated rosin. Given that many plant rosin compounds (e.g., rosin acids) are unsaturated, they tend to be oxidatively unstable and may undergo color changes upon storage. Hydrogenation can help to stabilize the rosins and reduce undesirable color change. Furthermore, hydrogenated rosins tend to have lighter colors than the parent rosin, providing more formulation and aesthetic flexibility.

The plant rosins and/or rosin acids may be partially or fully hydrogenated. Below is a sample reaction for the partial and full hydrogenation of abietic acid.

The alcohol in the esterification reaction may be a mono-alcohol, a diol, or a polyol, preferably a diol or a polyol. Suitable mono-alcohols may include methanol, which when reacted with a rosin acid can form a rosin methyl ester. A suitable diol with two hydroxyl groups can include trieth-

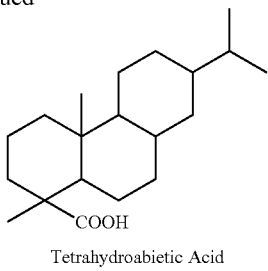

Tetrahydroabietic Acid

The treatment composition may comprise a plant rosin material is at least partially hydrogenated, preferably fully hydrogenated.

The plant rosin derivative may be both hydrogenated and esterified. For example, the plant rosin derivative may be a hydrogenated methyl ester or a hydrogenated glyceryl ester.

The plant rosin derivative may be a dimerized plant rosin. Dimerization may be useful for increasing the softening point and/or stability of a rosin acid. A sample dimerization reaction of abietic acid is shown below.

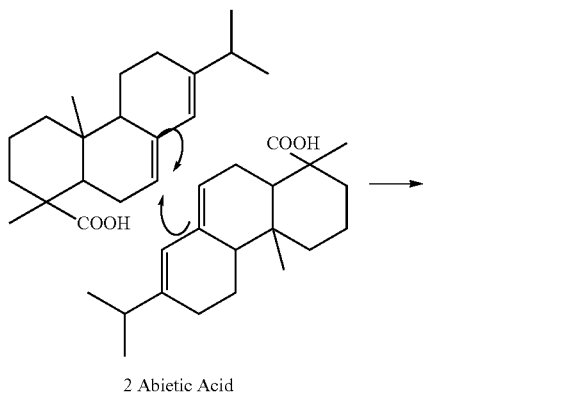

2 Abietic Acid

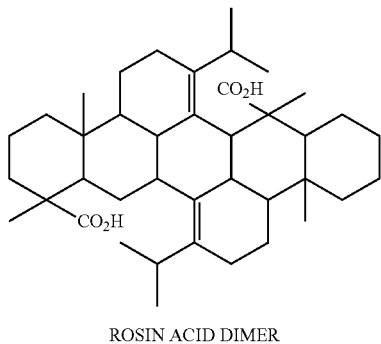

ROSIN ACID DIMER

As it is difficult or even impossible to completely dimerize a sample of rosins, rosin dimers are often present with undimerized rosin acids. Dimerized rosin acids may be further esterified.

A plant rosin derivative may dimerized through ions such as $Zi^{2+}$ or $Ca^{2+}$. For example, zine resinates are plant rosin derivatives where two abietic acid compounds are bound to a zine ion.

The plant rosin derivative may be a rosin-based polymer. As used here, in rosin-based polymer is intended to include compounds comprising rosin-based oligomers, including three or more monomeric units derived from rosin acids. The polymer may be a main-chain polymer or a side-chain polymer.

The plant rosin derivative may be a rosin soap, where a rosin acid is reacted with an alkali metal hydroxide (e.g., NaOH or KOH) or an alkaline earth metal hydroxide (e.g., $Ca(OH)_2$). More broadly, the plant rosin derivative may be the salt of a rosin acid.

The plant rosin derivative may be a functionalized plant rosin. In other word, the plant rosin may be functionalized, where one or more functional groups are added to the plant rosin.

A plant rosin derivative may include the product of a Diels-Alder reaction, such as the reaction product of a rosin acid and maleic anhydride; such reaction products may be polymerized.

A plant rosin derivative may include phenolic rosins, where a rosin is reacted with a phenol. A plant rosin derivative may include a rosin alcohol, wherein one or more of the carboxyl groups of the rosin acid are converted to hydroxyl groups.

Commercially available plant rosin derivatives that are suitable for the presently disclosed compositions and processes may include those disclosed in Example 1 of the Examples section below.

b. Benefit Agent

The particles of the present disclosure comprise one or more benefit agents. As described above, it is believed that the benefit agents become embedded and/or encapsulated in plant rosin material when the particles are formed. The particle formation can thus lead to improved stability, delivery, and/or performance of the benefit agent on a target surface, such as a fabric or hard surface. For example, such embedding and/or encapsulation of a benefit agent may prevent degradation of the benefit agent and/or undesirable interactions with other components of the liquid consumer product.

The compositions of the present disclosure may include the benefit agent and/or particles containing the benefit at a level at which the benefit agent provides its intended benefit when the composition is used as intended. For example, the benefit agent of the particles may be present at a level of from about 0.05% to about 10%, or from about 0.05% to about 5%, or from about 0.10% to about 4%, by weight of the composition.

The benefit agent may be selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, antiperspirant actives, emollients, skin sensates, and mixtures thereof. Particularly preferred benefit agents for the particles include fragrance materials.

The delivery efficacy of the benefit agent may be most efficacious when the benefit agent is relatively hydrophobic.

The benefit agent of the particles may include fragrance material, which may comprise one or more perfume raw materials. The term "perfume raw material" (or "PRM") as used herein refers to compounds having a molecular weight of at least about 100 g/mol and which are useful in imparting an odor, fragrance, essence, or scent, either alone or with other perfume raw materials. Typical PRMs comprise inter alia alcohols, ketones, aldehydes, esters, ethers, nitrites, and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

Suitable perfume raw materials may include materials such as geraniol, linalool, linalyl acetate, pyranol, geranyl acetate, anisaldehyde, citral, citronellal, lysmeral, citronellol, rose oxide, tetrahydrolinalool, hydroxycitronellal, betaionone, menthol, cinnamaldehyde, anethole, vanillin, ethyl vanillin, eugenol, cinnamon oil, carvone, piperonal, and mixtures thereof. The perfume raw materials may include naturally derived materials, such as essential oils.

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below. A perfume having a variety of PRMs from different quadrants may be desirable, for example, to provide fragrance benefits at different touchpoints during normal usage.

The perfume raw materials may comprise a perfume raw material selected from the group consisting of perfume raw materials having a boiling point (B.P.) lower than about 250° C. and a Log P lower than about 3, perfume raw materials having a B.P. of greater than about 250° C. and a Log P of greater than about 3, perfume raw materials having a B.P. of greater than about 250° C. and a Log P lower than about 3, perfume raw materials having a B.P. lower than about 250° C. and a Log P greater than about 3 and mixtures thereof. Perfume raw materials having a boiling point B.P. lower than about 250° C. and a Log P lower than about 3 are known as Quadrant I perfume raw materials. Quadrant 1 perfume raw materials are preferably limited to less than 30% of the perfume composition. Perfume raw materials having a B.P. of greater than about 250° C. and a Log P of greater than about 3 are known as Quadrant IV perfume raw materials, perfume raw materials having a B.P. of greater than about 250° C. and a Log P lower than about 3 are known as Quadrant II perfume raw materials, perfume raw materials having a B.P. lower than about 250° C. and a Log P greater than about 3 are known as a Quadrant III perfume raw materials. Suitable Quadrant I, II, III and IV perfume raw materials are disclosed in U.S. Pat. No. 6,869,923 B1.

The treatment composition may comprise particles where the benefit agent comprises fragrance material, where the fragrance material comprises from about 1% to about 40%, by weight of the fragrance material, of Quadrant I perfume raw materials, and/or from about 60% to about 99%, by weight of the fragrance material, of non-Quadrant I perfume raw materials.

The particles of the present disclosure may be particularly useful for helping to effectively solubilize certain perfume raw materials in aqueous consumer product compositions, especially those that are relatively low in surfactant, thereby avoiding emulsifiers or other processing steps. In particular, the delivery particles of the present disclosure are useful when the benefit agent of the particles contain hydrophobic perfume raw materials. The hydrophobic perfume raw materials may be characterized by a relatively high log P value, for example a log P of greater than about 3.0, and may include what is described above as Quadrant III PRMs, Quadrant IV PRMs, or mixtures thereof. The benefit agent of the particles may comprise at least about 50%, or at least about 60%, or at least about 70%, or at least about 80%, or at least about 90%, or about 100%, by weight of the benefit agent, of Quadrant III PRMs, Quadrant IV PRMs, or mixtures thereof. Compositions that comprise such levels of Quadrant III and/or IV PRMs as the benefit agent of the particles may be aqueous and comprise at least 60%, or at least 70%, or at least 80%, or at least 90%, or at least 95%, or at least 97%, by weight of the composition, of water, and/or less than 10%, or less than 5%, or less than 3%, surfactant.

Non-limiting examples of Quadrant III PRMs include iso-bomyl acetate, carvacrol, alpha-citronellol, paracymene, dihydro myrcenol, geranyl acetate, d-limonene, linalyl acetate, vertenex, and mixtures thereof.

Non-limiting examples of Quadrant IV (or enduring) PRMs include allyl cyclohexane propionate, ambrettolide, amyl benzoate, amyl cinnamate, amyl cinnamic aldehyde, amyl cinnamic aldehyde dimethyl acetal, iso-amyl salicylate, hydroxycitronellal-methyl anthranilate (known as Aurantiol®), benzophenone, benzyl salicylate, para-tert-butyl cyclohexyl acetate, iso-butyl quinoline, beta-caryophyllene, cadinene, cedrol, cedryl acetate, cedryl formate, cinnamyl cinnamate, cyclohexyl salicylate, cyclamen aldehyde, dihydro isojasmonate, diphenyl methane, diphenyl oxide, dodecalactone, 1-(1,2,3,4,5,6,7,8-octahydro-2,3,8,8-tetramethyl-2-naphthalenyl)-ethanone (known as iso E super®), ethylene brassylate, methyl phenyl glycidate, ethyl undecylenate, 15-hydroxypentadecanoic acid lactone (known as Exaltolide®), 1,3,4,6,7,8-hexahydro-4,6,6,7,8,8-hexamethyl-cyclopenta-gamma-2-benzopyran (known as Galaxolide®), geranyl anthranilate, geranyl phenyl acetate, hexadecanolide, hexenyl salicylate, hexyl cinnamic aldehyde, hexyl salicylate, alpha-irone, gamma-ionone, gamma-n-methyl ionone, para-tertiary-butyl-alpha-methyl hydrocinnamic aldehyde (known as lilial@), lilial (p-t-bucinal)®, linalyl benzoate, 2-methoxy naphthalene, methyl dihydrojasmone, musk indanone, musk ketone, musk tibetine, myristicin, oxahexadecanolide-10, oxahexadecanolide-11, patchouli alcohol, 5-acetyl-1,1,2,3,3,6-hexamethylindan (known as phantolide@), phenyl ethyl benzoate, phenylethylphenylacetate, phenyl heptanol, phenyl hexanol, alpha-santalol, delta-undecalactone, gamma-undecalactone, vetiveryl acetate, yara-yara, ylangene, and mixtures thereof.

c. Premix

The plant rosin material may be combined with the one or more benefit agents in a premix. The premix may be added to a base composition, which may comprise an adjunct ingredient, to form the treatment composition. The treatment composition of the present disclosure may comprise a premix, where the premix comprises plant rosin material and one or more benefit agents, as described in more detail below.

The premix may comprise from about 1% to about 99%, by weight of the premix, of the plant rosin material. The premix may comprise from about 1% to about 99%, by weight of the premix, of the benefit agent. The premix may comprise the plant rosin material and the benefit agent in a weight ratio of from about 1:99 to about 99:1, preferably from about 5:95 to about 95:5, more preferably from about 10:90 to about 90:10, more preferably from about 20:80 to about 80:20, more preferably from about 30:70 to about 80:20, more preferably from about 40:60 to about 80:20. It is believed that the performance benefit increases with higher plant rosin benefit agent weight ratios.

The premix may comprise an emulsifying agent. The premix may comprise from about 1% to about 95%, or from about 5% to about 95%, preferably from about 5% to about 40% by weight of the premix, of the emulsifying agent. The premix may comprise the plant rosin material and the emulsifying agent in a weight ratio of from about 5:95 to about 95:5. The premix may comprise the benefit agent and the emulsifying agent in a weight ratio of from about 5:95 to about 95:5. Suitable emulsifying agents may include surfactants, amphiphilic polymers, or mixtures thereof.

Suitable surfactants may include nonionic surfactants, anionic surfactants, or mixtures thereof, preferably nonionic surfactants. Suitable nonionic surfactants may include alkoxylated surfactants, pyrrolidone-based surfactants (including alkyl pyrrolidones, preferably C12-alkyl pyrrolidones), alkyl polyglycosides, and mixture thereof. Preferable HLB value of the nonionic surfactant is from 3 to 12.5. Suitable commercially available nonionic surfactants may include Lutensol™ XP 40 (ex BASF), Lutensol™ XP 70 (ex BASF), Plurafac™ LF 224 (BASF), Plurafac™ LF 401 (BASF), Ecosurf™ EH 9 (DOW), Neodol™ surfactant (SHELL), Dobanol™ surfactants (SHELL), Surfadone™ LP-300 (ASHLAND, Planteren™ APG 600, or mixtures thereof.

Suitable amphiphilic polymers may include graft copolymers, such as poly(ethylene glycol)-poly(vinyl acetate) graft copolymer, polyvinyl caprolactam-polyvinyl acetate-polyethylene glycol graft copolymer, or mixtures thereof. Commercially available graft copolymers may include Sokalon® HP 22 or Soluplus®, both available from BASF.

The premix may be made by heating the plant rosin material. The plant rosin material may be heated to a temperature equal to or greater than the softening point of the plant rosin material. The premix may be made by combining the heated plant rosin material with the benefit agent, and mixing.

In order to favor the homogeneity of the premix, the mixing may take place in a heated oil bath set at a temperature equal to the softening point of the plant rosin material. As the samples become homogenous, the temperature can be progressively reduced, which helps to lower the risk of loss of volatile materials (e.g., evaporation of volatile PRMs).

A processing aid, for example an emulsifying agent as described above, can be added at any suitable point. Preferably, the emulsifying agent, if any, is combined with the plant rosin material prior to adding the benefit agent (e.g., perfume). It is believed that this order of addition improves the ease of homogenization of the mixture.

As an additional or alternative step to heating, the plant rosin material may be grinded to small particles and mixed with the benefit agent.

Once made, the premix may be stored at ambient temperatures. That being said, when using the premix to make a final product composition, the premix may be heated, for example heated to around 60° C., before being injected in the finished product or otherwise combined with a base composition. This heating step is most likely to be helpful when the premix is characterized by a relatively high rosin:benefit agent (e.g. perfume) weight ratio, such as greater than 50:50. When the premix comprises a nonionic surfactant, for example as an emulsifying agent, the heating step may not be required.

Water

The liquid treatment compositions of the present disclosure may comprise water. The liquid treatment composition according to the present disclosure may comprise at least 8% water, preferably at least 25% water, more preferably at least 50% water, more preferably at least 60% water, more preferably at least 70% water, more preferably at least 75% water, more preferably at least 80% water, more preferably at least 90% water, by weight of the treatment composition.

The liquid treatment compositions according to the present disclosure may comprise from about 1% to about 99%, or 10% to 99%, or from about 10% to about 96%, or from about 12% to about 90%, or from about 20% to about 80%, or from about 40% to about 80%, by weight of the composition, of water.

The liquid consumer product compositions of the present disclosure may contain relatively high amounts of water, such as greater than 50%, or greater than 60%, or greater than 70%, or greater than 80%, or greater than 90%, water. In particular, liquid compositions such as heavy-duty laundry detergents, liquid fabric conditioners (e.g., softeners or enhancers), and liquid hard surface cleaners may advantageously be formulated with high levels of water, for example to enhance flowability or dispersibility.

The compositions of the present disclosure may comprise less than 50 wt %, or less than 40 wt %, or less than 30 wt %, or less than 20 wt %, or less than 15 wt %, or less than 12 wt %, or less than 10 wt %, by weight of the composition, of water.

The liquid compositions of the present disclosure may be substantially non-aqueous, and may comprise less than 10 wt %, or less than 5 wt %, or less than 3 wt %, or less than 1 wt %, or less than 0.1 wt %, or even 0 wt %, by weight of the composition, of water.

The water level may depend on the form and/or intended use of the composition. For example, when the composition is in the form of a unit dose composition (for example, a liquid composition encapsulated by a water-soluble film), the water, may be present at a level of from about 1% to about 20%, or from about 5% to about 15%; when the composition is in the form of a compact liquid laundry detergent, the water, may be present at a level of from about 10% to about 50%, or from about 20% to about 40%.

Adjunct Ingredients

The treatment compositions of the present disclosure may further include an adjunct ingredient in addition to the particles of the present disclosure. The adjuncts may be suitable for delivering a treatment benefit to a target surface, such as a fabric or other textile. Adjuncts ingredients, as used herein, may also include agents that facilitate chemical or physical stability in the treatment compositions, such as buffers, structurants/thickeners, and/or carriers.

The adjunct ingredient(s) may be present in the composition at levels suitable for the intended use of the composition. Typical usage levels range from as low as 0.001% by weight of composition for adjuncts such as optical brighteners to 50% by weight of composition for builders.

The adjunct ingredient may include an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softeners, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof. The compositions of the present disclosure may include, among other things, an amine, a surfactant system, a conditioning agent, a water-binding agent, a sulfite, a structurant, organic solvent, free perfume, a perfume delivery system, or mixtures thereof. Several of these adjuncts are described in more detail below.

The consumer product adjunct may comprise a surfactant system, conditioning actives, or combinations thereof. Preferably, the surfactant system comprises anionic surfactant, nonionic surfactant, cationic surfactant, and/or zwitterionic surfactant. Preferably, the fabric softening agents comprise a quaternary ammonium compound, silicone compounds, or both.

Liquid consumer product compositions according to the present disclosure may include a surfactant system. The surfactant system may consist of one type of surfactant. The surfactant system may include more than one surfactant.

The compositions of the present disclosure may include from about 20% to about 75%, or from about 25% to about 70%, or from about 30% to about 50%, by weight of the composition, of a surfactant system. Compositions of the present disclosure may include less than 20%, or less than 10%, or less than 5%, or less than 3%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES) including sodium laureth sulfate (SLES), alkyl sulfates (AS) including sodium lauryl sulfate (SLS), or mixtures thereof. Other suitable anionic surfactants include branched modified alkyl benzene sulfonates (MLAS), methyl ester sulfonates (MES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine). In certain treatment compositions, for example, those that include a cationic material such as a fabric conditioning agent, it may be desirable to limit the amount of anionic surfactant present; for example, the treatment composition may comprise less than 5%, or less than 3%, or less than 1%, or less than 0.1%, or even 0%, by weight of the treatment composition, of anionic surfactant.

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branhed alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

The compositions of the present disclosure may include a conditioning active. Compositions that contain conditioning actives may provide softness, anti-wrinkle, anti-static, conditioning, anti-stretch, color, and/or appearance benefits. Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof. Preferably, the treatment composition comprises a conditioning active that comprises a quaternary ammonium ester compound, more preferably a quaternary ammonium ester compound in combination with a silicone.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Liquid treatment compositions according to the present disclosure may include an external structurant. External structurants can provide physical stability to liquid compositions according to the present disclosure, for example by helping to suspend the delivery particles. Structurants, when present, are preferably present in an effective amount that is capable of suspending the particles in the treatment composition. External structurants may include non-polymeric crystalline, hydroxy-functional structurants and/or polymeric structurants.

Non-polymeric crystalline, hydroxyl functional structurants may comprise a crystallizable glyceride, which may be pre-emulsified to aid dispersion into the final detergent composition. Suitable crystallizable glycerides include hydrogenated castor oil or "HCO" or derivatives thereof, provided that it is capable of crystallizing in the liquid detergent composition.

Polymeric structurants may include naturally derived structurants and/or synthetic structurants. Naturally derived polymeric structurants include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. The structurant may comprise cellulosic fibers, for example in the form of microfibrillated cellulose. Cellulose may be derived from bacterial, wood, or other plants such as fruit or sugar beet.

Synthetic polymeric structurants include: polycarboxylates, polyacrylates, hydrophobically modified ethoxylated urethanes, hydrophobically modified non-ionic polyols and mixtures thereof. The polycarboxylate polymer may be a polyacrylate, polymethacrylate or mixtures thereof. The polyacrylate may be a copolymer of unsaturated mono- or di-carbonic acid and $C_1$-$C_{30}$ alkyl ester of the (meth)acrylic acid. Such copolymers are available from Lubrizol Corp. under the tradename Carbopol® Aqua 30.

The compositions of the present disclosure may include solvent, preferably organic solvent, such as a non-amino-functional organic solvent. Suitable organic solvents may include glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof. Organic solvents can provide physical stability benefits, particularly in compact formulations having relatively low water levels. The compositions of the present disclosure may include from about 5% to about 80%, or from about 10% to about 50%, by weight of the composition, of organic solvent.

The compositions of the present disclosure may include additional aesthetic agents, such as those selected from dyes, opacifiers, pearlescent agents, or mixtures thereof.

Liquid consumer product compositions according to the present disclosure may include a perfume delivery system. Suitable perfume delivery systems may include core-shell encapsulates, pro-perfumes (such as amine- and/or silicone-based pro-perfumes), and mixtures thereof. Core-shell encapsulates may comprise a core and a shell surrounding the core. The core may comprise a benefit agent such as perfume, and optionally a partitioning modifier such as isopropyl myristate. The shell may comprise a polymer, for example melamine formaldehyde, polyurea, polyvinyl alcohol, polyacrylate, or a polysaccharide. Suitable encapsulates may be characterized by a volume-weighted median particle size of from about 10 microns to about 100 microns, or from about 10 microns to about 50 microns, or from about 15 microns to about 40 microns. Perfume delivery systems may provide benefits such as improved perfume stability, deposition, and/or longevity, and may be particularly useful for perfume raw materials that do not associate well with the plant rosin materials of the present disclosure.

When the consumer product composition is in the form of a unit dose article, such as a pouch or a sachet, the composition may be encapsulated by a water-soluble film. A water-soluble unit dose article may comprise at least one water-soluble film shaped such that the unit-dose article comprises at least one internal compartment surrounded by the water-soluble film. The at least one compartment comprises the detergent composition.

The unit dose article may comprise more than one compartment, even at least two compartments, or even at least three compartments, or even at least four compartments, or even at least five compartments. The compartments may be arranged in superposed orientation, i.e. one positioned on top of the other. Alternatively, the compartments may be positioned in a side-by-side orientation, i.e. one orientated next to the other. The compartments may even be orientated in a "tire and rim" arrangement, i.e. a first compartment is positioned next to a second compartment, but the first compartment at least partially surrounds the second compartment, but does not completely enclose the second compartment. Alternatively, one compartment may be completely enclosed within another compartment. When one compartment comprises a liquid composition according to the present disclosure, another compartment may comprise a solid, a liquid, or a mixture thereof.

The film of the present invention may be soluble or dispersible in water (e.g., at 20° C.). Preferred film materials include polymeric materials. The film material can, for example, be obtained by casting, blow-moulding, extrusion or blown extrusion of the polymeric material, as known in the art. Preferably, the water-soluble film comprises polyvinyl alcohol polymer or copolymer, preferably a blend of polyvinylalcohol polymers and/or polyvinylalcohol copolymers, preferably selected from sulphonated and carboxylated anionic polyvinylalcohol copolymers especially carboxylated anionic polyvinylalcohol copolymers, most preferably a blend of a polyvinylalcohol homopolymer and a carboxylated anionic polyvinylalcohol copolymer. Suitable films include those supplied by MonoSol, LLC (Indiana) under the trade references M8630, M8900, M8779, and/or M8310. The film may comprise an aversive agent, for example a bittering agent. Prior to be being formed into a unit dose article, the water-soluble film preferably has a thickness of from 20 to 150 microns, preferably 35 to 125 microns, even more preferably 50 to 110 microns, most preferably about 76 microns.

Process of Making

The present disclosure also relates to processes for making liquid treatment compositions. The process of making a liquid treatment composition, which may be a consumer product composition, may comprise the step of combining the ingredients (e.g., a plant rosin material, one or more benefit agents, and an adjunct material) as described herein.

The process of making a liquid treatment composition according to the present disclosure may comprise the steps of combining the plant rosin material and the one or more benefit agents as separate ingredients (e.g., without premixing the plant rosin material and the one or more benefit agents) with a liquid base composition, where the liquid base composition comprises an adjunct ingredient.

The process of making a liquid treatment composition according to the present disclosure may include the step of providing a premix. The premix may comprise the plant rosin material and the one or more benefit agents. The premix may be combined with a liquid base composition. The liquid base composition may comprise the adjunct ingredient.

The liquid treatment compositions of the present disclosure can be formulated into any suitable form and prepared by any process chosen by the formulator. The materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders.

The liquid treatment composition may be encapsulated in water-soluble film(s) according to known methods to form a unitized dose article.

The liquid treatment composition may be placed into an aerosol or other spray container according to known methods.

Process of Treating a Surface

The present disclosure also relates to a process of treating a surface, such as a fabric, hair, and/or skin. The process may include the step of contacting a surface with a treatment composition according to the present disclosure.

The contacting step may occur in the presence of water. The processes of the present disclosure may include diluting the compact liquid detergent composition with water to form a treatment liquor, which may contact the surface to be treated. The compact liquid detergent composition may be diluted from 100-fold to 1000-fold, or from 200-fold to 900-fold, or from 300-fold to 800-fold, by water.

The contacting step may occur in the drum of an automatic washing machine. The contacting step may occur as a pretreatment step.

Combinations

Specifically contemplated combinations of the disclosure are herein described in the following lettered paragraphs. These combinations are intended to be illustrative in nature and are not intended to be limiting.

A. A liquid treatment composition comprising particles and an adjunct ingredient, wherein the particles comprise a plant rosin material and one or more benefit agents.

B. The liquid treatment composition according to paragraph A, wherein the particles are characterized by a volume-weighted median particle size of from about from about 10 microns to about 400 microns, or from about 15 microns to about 300 microns, or from about 20 microns to about 250 microns, or from about 25 microns to about 200 microns, or from about 30 microns to about 150 microns, or from about 35 to about 125 microns, preferably from about 40 to about 100 microns, more preferably from about 50 to about 90 microns.

C. The liquid treatment composition according to any of paragraphs A or B, wherein the plant rosin material and the one or more benefit agents are present in the particles in a weight ratio of from about 5:95 to about 95:5, preferably from about 20:80 to about 80:20, more preferably from about 30:70 to about 70:30, more preferably from about 40:60 to about 60:40.

D. The liquid treatment composition according to any of paragraphs A-C, wherein the plant rosin material comprises a material selected from the group consisting of gum rosin, wood rosin, tall oil rosin, derivatives thereof, and mixtures thereof, preferably gum rosin, derivatives thereof, and mixtures thereof, more preferably a gum rosin ester.

E. The liquid treatment composition according to any of paragraphs A-D, wherein the plant rosin material is a plant rosin ester, preferably an ester formed from an alcohol having two or more carbon atoms, more preferably where the alcohol is glycerol, pentaerythritol, or a mixture thereof.

F. The liquid treatment composition according to any of paragraphs A-E, wherein the plant rosin material is at least partially hydrogenated, preferably fully hydrogenated.

G. The liquid treatment composition according to any of paragraphs A-F, wherein the plant rosin material comprises at least 50%, more preferably at least 60%, more preferably at least 70%, more preferably at least 80%, more preferably at least 85%, by weight of the plant rosin material, of an abietic-type acid, a derivative of an abietic-type acid, or a mixture thereof.

H. The liquid treatment composition according to any of paragraphs A-G, wherein the plant rosin material is characterized by a softening point of from about 50° C. to about 175° C., preferably from about 60° C. to about 150° C., more preferably from about 75° C. to about 125° C.

I. The liquid treatment composition according to any of paragraphs A-H, wherein the plant rosin material is characterized by an acid number of less than about 175, preferably less than about 125, preferably less than about 100, more preferably less than about 75, even more preferably less than about 50, more preferably less than about 25.

J. The liquid treatment composition according to any of paragraphs A-I, wherein the plant rosin material is characterized by a color grade of from about 1 to about 10, or from about 1 to about 8, as graded on the Gardner Color standard number.

K. The liquid treatment composition according to any of paragraphs A-J, wherein the one or more benefit agents is selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, antiperspirant actives, emollients, skin sensates, and mixtures thereof, preferably selected from fragrance materials.

L. The liquid treatment composition according to any of paragraphs A-K, wherein the one or more benefit agents comprises a fragrance material.

M. The liquid treatment composition according to any of paragraphs A-L, wherein the fragrance material comprises from about T % to about 40%, by weight of the fragrance material, of Quadrant I perfume raw materials, and/or from about 60% to about 99%, by weight of the fragrance material, of non-Quadrant I perfume raw materials.

N. The liquid treatment composition according to any of paragraphs A-M, wherein the one or more benefit agents are encapsulated in the plant rosin material, and/or are partially embedded in the plant rosin material.

O. The liquid treatment composition according to any of paragraphs A-N, wherein the liquid treatment composition is formed by a process comprising adding a premix to a base composition, wherein the premix comprises the plant rosin material and the one or more benefit agents.

P. The liquid treatment composition according to any of paragraphs A-O, wherein the adjunct ingredient is selected from an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof.

Q. The liquid treatment composition according to any of paragraphs A-P, wherein the adjunct ingredient comprises a surfactant system, fabric softening agents, or combinations thereof, preferably wherein the surfactant system comprises anionic surfactant, nonionic surfactant, cationic surfactant, and/or zwitterionic surfactant, and/or preferably wherein the fabric softening agents comprise a quaternary ammonium compound, silicone compounds, or both.

R. The liquid treatment composition according to any of paragraphs A-Q, wherein the liquid treatment composition further comprises an amphiphilic polymer, preferably an amphiphilic graft co-polymer, more preferably an amphiphilic graft co-polymer comprising a polyalkylene glycol as a graft base and one or more side chains, the side chains comprising vinyl acetate moieties and optional N-vinyl-caprolactam moieties.

S. The liquid treatment composition according to any of paragraphs A-R, wherein the liquid treatment composition comprises at least 8% water, preferably at least 25% water, more preferably at least 50% water, more preferably at least 60% water, more preferably at least 70% water, more preferably at least 75% water, more preferably at least 80% water, more preferably at least 90% water, by weight of the liquid treatment composition.

T. The liquid treatment composition according to any of paragraphs A-S, wherein the liquid treatment composition has a viscosity of from 1 to 1500 centipoises (1-1500 mPa*s) at 20 s$^{-1}$ and 21° C.

U. The liquid treatment composition according to any of paragraphs A-T, wherein the liquid treatment composition further comprises a structurant, preferably present in an effective amount that is capable of suspending the particles in the liquid treatment composition.

V. The liquid treatment composition according to any of paragraphs A-U, wherein the liquid treatment composition is a consumer product composition, preferably a fabric care composition, a hard surface cleaner composition, a dish care composition, a hair care composition, a body cleansing composition, or a mixture thereof, preferably wherein the fabric care composition is a fabric detergent composition, a fabric conditioning composition, or a mixture thereof.

W. The liquid treatment composition according to any of paragraphs A-V, wherein the liquid treatment composition is encapsulated in a water-soluble film.

X. A liquid treatment composition comprising particles and an adjunct ingredient, wherein the particles comprise a tricyclic diterpene monocarboxylic acid, a derivative thereof, or a mixture thereof, wherein the particles further comprise one or more benefit agents, preferably wherein the tricyclic diterpene monocarboxylic acid, the derivative thereof, or the mixture thereof comprises a material selected from the group consisting of abietic-type acids, derivatives thereof, pimaric-type acids, derivatives thereof, and mixtures thereof, more preferably wherein the tricyclic diterpene monocarboxylic acid comprises a derivative in the form of an ester.

Y. A method of treating a surface, preferably a fabric, the method comprising the step of contacting the surface with the liquid treatment composition according to any of paragraphs A-X, optionally in the presence of water.

Test Methods

It is understood that the test methods that are disclosed in the Test Methods Section of the present application should be used to determine the respective values of the parameters of Applicant's claimed subject matter as claimed and described herein.

Test Method for Determining the Logarithm of the Octanol/Water Partition Coefficient (Log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Softening Point Test Method

If available, the softening point of a plant rosin material as provided by the manufacturer/supplier is to be used.

If not available from the manufacturer/supplier, the softening point is determined according to ASTM E28-18, "Standard Test Methods for Softening Point of Resins Derived from Pine Chemicals," using the version approved Jul. 1, 2018, and published July 2018. More specifically, the Reference Method ("Automated Ring and Ball Softening Point Method") provided therein is to be followed. The method is summarized here.

As used herein (and as described in ASTM E28-18), the softening point is defined as the temperature at which a disk of the sample held with a horizontal ring (brass shouldered ring; 19.8 mm inner ring diameter, 23.0 outer diameter, as indicated in the ASTM method) is forced downward a distance of 25.4 mm (1 in.) under the weight of a steel ball (9.53 mm diameter; mass between 3.45 and 3.55 g) as the sample is heated at 5 C/min in a water, glycerin, silicone oil, ethylene glycol/water, or glycerin/water bath.

Sample Preparation: Select a representative sample of the rosin material to be tested. The sample should include flakes, pastilles, or freshly broken lumps free of oxidized surfaces; avoid inclusion of finely divided material or dust. Melt the sample in a clean container; avoid overheating, and avoid incorporating air bubbles into the sample. The time from the beginning of heating to the pouring of the sample should not exceed 15 minutes. Rest the ring, bottom down, on a metal surface; the ring may be preheated. Pour the melted rosin sample into the ring so as to leave an excess upon cooling. After cooling for at least 30 minutes, remove excess material from the periphery and top of the ring.

Bath Liquid: The selection of the bath liquid will depend on the softening point ("SP") of the rosin material. For SPs between 35 C and 80 C, use water (distilled or deionized, freshly boiled). For SPs between 80 C and 150 C, use USP Glycerin. For SPs above 80 C, use Silicone Oil (Polydimethylsiloxane—200 fluid, 50 cSt, from Dow Corning, Midland, Mich.). For SPs up to 35 C, use a 50/50 (v/v) mixture of Ethylene Glycol and Distilled Water; the bath should be cooled to −25 C in a precooled freezer or an isopropyl dry-ice bath.

Test: Use a suitable automated ring and ball-softening point instrument with control unit; calibrate according to the manufacturer's instructions. Provide a stir bar to a 600 mL beaker and fill with a bath liquid as provided above, depending on the softening point of the rosin material. Set up the apparatus, ring, ball, test insert, support pins as recommended by the manufacturer's instructions. Verify that the control unit is set for the correct bath liquid.

Heat the bath so that the temperature of the bath liquid is raised uniformly at a rate of 5 C/min. The test is complete when then light beam has been interrupted by the falling ball and material. Record the softening point at the temperature displayed on the unit after the test is completed.

Acid Number Test Method

If available, the acid number of a plant rosin material as provided by the manufacturer/supplier is to be used.

If not available from the manufacturer/supplier, the acid value is determined according to ASTM D465-15 (Reapproved 2020), "Standard Test Methods for Acid Number of Pine Chemical Products Including Tall Oil and Other Related Products," as approved Jun. 1, 2020 and published June, 2020. More specifically, the Referee Method ("Potentiometric Method") provided therein is to be followed. The method is summarized here.

Provide freshly chipped samples of rosin material, which may be further crushed to facilitate weighing and dissolution; pieces with oxidized surfaces, as well as existing rosin dust or powder, should not be used. If a nonhomogenous liquid, place in a closed container with a capillary vent or its equivalent, and heat in a hot water bath; the sample may be agitated during heat, and used after homogenous and well stirred.

Based on the following table, transfer the proscribed amount of sample to a 400 mL tall-form beaker; add the proper amount of solvent I and swirl to dissolve, heating gently if necessary. Add the proper amount of solvent II, if required, and cool to near room temperature. Immerse each electrode of a glass electrode pH meter (calibrated/standardized according to the manufacturer's instructions) in the solution. Stir with a stir bar.

Titrate with a standard alkali solution (a 0.5 N or 0.1 N KOH solution), recording the buret and pH meter readings. Sufficient alkali may be added to bring the pH of the solution to about 8. Add alkali in 1.0 mL portions until the change in pH per increment added amounts to about 0.3 pH unit. Reduce the additions of alkali to 0.1 mL or smaller until the end point has been passed, as indicated by a significant decrease in pH units er 0.1 mL added. Continue the titration with 1.0 mL portions until it becomes apparent that the inflection point has been well defined.

Determine the inflection point (point of maximum change in pH per mL of alkali solution) to the nearest 0.05 mL by plotting the pH readings against the milliliters of alkali used. (For greater accuracy, the chance in pH per mL may be plotted against the pH; the peak corresponds to the inflection point.) The inflection point is considered the end point of the titration.

The acid number of the sample, expressed as milligrams of KOH per gram of sample is calculated as follows, and may be reported to the nearest whole number:

$$\text{Acid Number} = (A \times N \times 56.1)/B$$

where: A=alkali solution (in mL) required for titration of the specimen; N=normality of the alkali solution, and B=specimen weight (in grams).

Color Grade Test Method (Gardner Color)

If available, the color grade (Gardner color) of a plant rosin as provided by the manufacturer/supplier is to be used.

If not available from the manufacturer/supplier, the color grade (Gardner color) is determined according to ASTM D6166-12 (Reapproved 2016), "Standard Test Method for Color of Pine Chemicals and Related Products (Instrumental Determination of Gardner Color)," as approved Dec. 1, 2016, and published December, 2016. The method is summarized here.

The color of a liquid sample is measured using an instrument, such as a Gardner Color Comparator L, 115V (ex. BYK), capable of measuring transmitted color and reporting in Gardner colors (or, less preferred, in a color system that can be converted to Gardner colors by known methods, such as those disclosed in the ASTM D6166-12). The instrument is calibrated according to the manufacturer's instructions.

To prepare the rosin sample for color analysis, a molten sample of the rosin material is introduced to a glass cuvet (10-mm path, unless a different path length is specified by the instrument manufacturer). If the sample is solid, it should comprise freshly broken lumps and be free of dust and finely divided material; the solid should be melted (e.g. in 15 minutes or less, in an oven, sand bath, or oil bath), taking care to avoid overheating and introduction of bubbles. After the molten sample is introduced to the glass cuvet, measurements should be taken while still molten. If the material is cloudy, it should be filtered.

The glass cuvet is inserted into the instrument, and the color is measured by following the manufacturer's instructions.

Flash Point Test Method

If available, the flash point of a plant rosin as provided by the manufacturer/supplier is to be used.

If not available from the manufacturer/supplier, the flash point is determined according to ASTM D92-18, "Standard Test Methods for Flash and Fire Points by Cleveland Open Cup Tester," as approved Jul. 1, 2018, and published July, 2018.

Test Method for Determining Amounts of Major Rosin Acid Isomers

If available, the amounts of the major rosin acid isomers of a plant rosin as provided by the manufacturer/supplier is to be used.

If not available from the manufacturer/supplier, the amounts of the major rosin acid isomers are determined according to ASTM D5974-15, "Standard Test Method for Fatty and Rosin Acids in Tall Oil Fractionation Products by Capillary Gas Chromatography," as approved Jul. 1, 2015, and published August, 2015. The method is summarized here.

This method uses gas chromatography to determine the levels of, for example, rosin acids present in a rosin sample. Prior to chromatographic separation, certain free acids should be converted to more volatile and more stable methyl esters. For rosin acids, this conversion may take place by means of tetramethylammonium hydroxide (TMAH).

To prepare the methyl ester, a rosin sample (if solid, freshly broken to avoid oxidation) is dissolved in 0.5-3.0 mL of a 50:50 ether/methanol mixture (and optionally 2 to 3 drops of toluene), 2 to 3 drops of phenolphthalein indicator solution is added. The mixture is titrated to a pH of 7.9 to 8.1, or to the very first permanent pink color, with a 6% solution of TMAH. If over-titrated, the mixture may be back-titrated with a 5% acetic acid solution (v/v) in methanol. When the solution is injected into the heated injection port of the chromatograph, the tetramethylammonium salts are pyrolyzed to methyl esters.

A gas chromatograph (GC) equipped with a flame ionization detector (FID) is used and operated under the following conditions: Column temperature (oven temperature)—initial, 150 C; hold, 5 min.; ramp, 5 C/min; final 250 C; hold 10 min; injection port temp., 300 C; injection port liner, glass split; detector temp., 325 C; carrier gas, helium; linear gas velocity, 19.5-20.5 cm/s; split ratio, 100 to 1 maximum; detector, FID; hydrogen, 30 mL/min; air, 400 mL/min; makeup gas, 30 mL/min. A high resolution column, preferably 30 m in length, 0.32 mm internal diameter, with a 0.20-µm film thickness of bicyanopropylsiloxane-type liquid, is used.

Prepare calibration standards of myristic acid and high-purity standards of rosin acids that are expected to be present, record the weights, and convert to methyl esters as described above. To prepare the test sample, accurately weigh about 50 mg of sample and about 15 mg of myristic acid in a suitable vial, record the weight, and convert to methyl esters as described above.

Use the calibration standards (injecting 0.5-1.0 µL) to calibrate the GC, recording the retention times and calculating the individual relative response factors. To analyze the test sample, inject 0.5-1.0 μL (diluting the sample with additional solvent if necessary), obtain the peak areas of all of the peaks needed from the chromatogram, and calculate the absolute value of each peak of interest. The relative percent of each rosin acid methyl ester present may be determined by dividing the peak area for the rosin acid methyl ester being determined by the sum of areas of all rosin acid methyl ester peaks.

Fabric Treatment Method

When treating fabrics with a composition according to the present disclosure in the experiments below, the following method is followed unless otherwise indicated. For each treatment, a washing machine (ex Miele) is loaded with about 3 kg of a fabric load. The fabric load comprises about 1065 g knitted cotton fabric and about 1065 g polyester-cotton fabrics (50/50). Additionally, the fabric load comprises twenty terry towel tracers, which weigh together about 870 g. The washing cycle is run at 95° C.

Prior to the test treatment, the load is preconditioned twice, each time using the 95° C. short cotton cycle with 79 g of unperfumed IEC A Base detergent (ex WFK Testgewebe GmbH), followed by two additional 95° C. washes without detergent.

For the test treatment, the load is washed using a 40° C. short cotton cycle, 1200 rpm spin speed with 79 g IEC A Base detergent, which is added at the start of the wash cycle in the appropriate dispenser. A dosage of 40 ml of the test fabric treatment composition is added in the appropriate dispenser.

Method to Determine Headspace Concentration Above Treated Fabrics

The fabric tracers from the abovementioned Fabric Treatment method may be analyzed via headspace analysis at least two specific touchpoints:

WFO (Wet Fabric Odor, or WET): Wet fabrics are analyzed after the fabric treatment method is finished.

DFO (Dry Fabric Odor, or DRY): Dried Fabrics are analyzed after the fabrics have been line-dried in a closed room for approximately twenty-four hours.

The headspace above the cotton terry tracers is analyzed using SPME headspace GC/MS (gas chromatography mass spectrometry) approach. 4 cm×4 cm aliquots of cotton tracers are transferred to 25 ml headspace vials. The fabric samples are equilibrated for 10 minutes at 65° C. The headspace above the fabrics is sampled via SPME (50/30 μm DVB/Carboxen/PDMS) for 5 minutes. The SPME fiber is subsequently on-line thermally desorbed into the GC. The analytes are analyzed by GC/MS in full scan mode. The total perfume HS response and perfume headspace composition above the tested legs can be determined.

Viscosity Method

Viscosity of a liquid composition is measured using a DV-E viscometer from Brookfield. The spindle is automatically spun at a rate of 60 rpm until a stable value is given in centipoise (cP).

Viscosity of the premix comprising rosin plant, delivery agent and potentially emulsifying agent is measured using a HAAKE MARS from Thermo Scientific using a 60 mm 1° C. one and a gap size of 52 micrometers. The shear viscosity at 20 s$^{-1}$ can be obtained from a logarithmic shear rate sweep from 0.01 s$^{-1}$ to 1200 s$^{-1}$ at 21° C. The viscosity may be expressed as centipoise (cP).

Particle Size Determination

Depending on the relative size of the particle, one of two methods is employed: image analysis if the approximate volume-weighted median particle size of the population is 10 μm or greater, or microscopy if the approximate volume-weighted median particle size of the population is less than 10 μm. These methods are described in more detail below.

A. Image Analysis

The volume-weighted median particle size is calculated from images taken from the sample flowing through a variable size flow cell. This instrument is specifically designed for image analysis device for liquid applications (Occhio FC200S). The sample is pumped via a syringe pump at very low speed through the flow cell, while the sample passes through the flow cell images are taken at set times. The speed is matched with the frame speed of the camera and it is dependent on the behaviour of the sample and the particles it contains. The flow cell sizes used were 250 and 500 μm and were depending on the size of the capsules. Detection of the capsules is done via grayscale threshold. Callisto version 2013.13 software is used to read out the pixels and calculate size and shape parameters. The size descriptor used is ISO area diameter.

Illumination is a red-led light source, adjustment of illumination is done manually until proper grayscale detection of the particles is possible. Hardware magnification is dependent on the size of the particles: 6× or 9×.

B. Microscopy

The volume-weighted median particle size of the particles is calculated from the values obtained by microscopically observing and measuring the diameter of around 900 capsules observed in randomly sampled aliquots. The microscope used is the Leica DM6000B. The magnification of the microscope is set to 200×. The outputs obtained after the microscopy analysis are: (1) list of diameters detected; and (2) counts per each diameter size detected.

Therefore, the volume (V) of each particle is calculated with the following equation:

$$V = \frac{4}{3}\pi r^3$$

where r is the radius of each detected particle. Finally, the volume-weighted median particle size is calculated (e.g., via a spreadsheet, such those created in Microsoft Excel™), assuming that each particle is a sphere.

EXAMPLES

The examples provided below are intended to be illustrative in nature and are not intended to be limiting.

Example 1. Exemplary Plant Rosin Materials

Table 1 shows a variety of commercially available plant rosin materials. Additional information is provided where available.

TABLE 1

Exemplary plant rosin materials

| No. | Rosin Type | Derivative Type | Additives | Softening Point (° C.) | Acid Value (mg KOH/g) | TRADE NAME | Mfr.* |
|---|---|---|---|---|---|---|---|
| 1 | Gum Rosin | — | — | 79 | 163 | — | A |
| 2 | Gum Rosin | Glycerol ester | — | 88 | 8 | Permalyn 5095 | B |
| 3 | Gum Rosin | Pentaerythritol ester | — | 125 | 13 | Lurefor 125 | A |

TABLE 1-continued

Exemplary plant rosin materials

| No. | Rosin Type | Derivative Type | Additives | Softening Point (° C.) | Acid Value (mg KOH/g) | TRADE NAME | Mfr.* |
|---|---|---|---|---|---|---|---|
| 4 | Gum Rosin | Pentaerythritol ester | — | 100 | 15 | Permalyn 5110 | B |
| 5 | Gum Rosin | Methyl ester | — | — | 5 | Abalyn D-E | C |
| 6 | Gum Rosin | Hydrogenated | — | 70 | 158 | Staybelite Resin-E | C |
| 7 | Misc. Rosin | Partially Hydrogenated | — | 75 | 168 | Foralyn E | C |
| 8 | Gum Rosin | Partially dimerized | — | 103 | 146 | Poly-Pale | C |
| 9 | Wood Rosin | Hydrogenated glycerol ester | — | 84 | 6 | Foral 85 | B |
| 10 | Wood Rosin | Hydrogenated pentaerythritol ester | — | 99 | 11 | Foral 105 | B |
| 11 | Tall Oil | Saponified sodium soap | — | — | 0.5 | Dresinate TX Rosin Soap | C |
| 12 | Misc. Rosin | Dimerized; Zinc resinate | Zinc salt | 160 | 5 | Zincogral Z | B |

*Mfr. = Manufacturer, according to the following key:
A—Luresa Resinas S.L.
B—DRT
C—Eastman Example 2. Exemplary Liquid Fabric Conditioning Product Comprising Particles The below LFE formulation in Table 2A is an example of liquid fabric enhancer product that comprises particles. The exemplary liquid fabric conditioning product is made by adding perfume and plant rosin material to a base composition via a premix comprising a 50:50 ratio of perfume and glycerol ester resin.

TABLE 2A

LFE formulation comprising capsules

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Particles resulting from plant rosin/perfume (50:50) feedstock composition | 2.0% |
| Water | Balance to 100% |

[1]Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])

a. Microscopy

Micrographs of the liquid product composition are taken with fluorescence confocal laser scanning microsopy (CLSM), at a magnification of 63×. FIG. 1 shows a representative micrograph, where particles having an approximate diameter of 5-14 microns are seen.

It is believed that the plant rosin material and perfume are co-located in the particles for at least the following reasons. First, the particles are visible under the optical/confocal microscope. The perfume can be dyed with coumarin, and by using different filters and detectors on the microscope, it is observed that the perfume is co-located with the particle. Furthermore, the presence of rosin material in the particle is confirmed by squeezing the particle with a microslide. When enough pressure is applied to collapse the particle, the rosin (observed as a stringy/sticky material) can be identified at the same location as the perfume.

b. Product Headspace

Furthermore, perfume concentrations can be analyzed in the headspace of the product composition. Compared to a nil-rosin formulation, it is found that there is less perfume in the headspace of the formulation that includes the rosin/perfume premix. This indicates that the rosin is interacting with the perfume, preventing it from evaporating out of the formulation and into the headspace.

c. Particle Size

Additionally, the presence of capsules in the finished liquid fabric enhancer product (e.g. generally according to the formula of Table 2A, with the amounts as varied below) can be evaluated via the Particle Size characterization methods described in the Test Method section. Depending on the size range of the particles, one of two methods is employed: image analysis or microscopy.

Legs 1, 2 and 3 differ in terms of the levels of resin, perfume, and emulsifying agent; the percentage levels provided below are by weight of the final product ("FP"). For Leg 1 and Leg 2, the presence of large particles required the Image analysis method, while for Leg 3, the particles were relatively smaller and therefore the Microscopy method was preferred. Particles sizes at various points of the volume-weighted particle size distribution (PSD) are provided in Table 2B. For each of the three legs, the median particle size (at 50% volume-weighted distribution) is reported in Table 2B.

TABLE 2B

| Leg # | Plant Rosin Material in FP | | Benefit Agent | | Emulsifying Agent | | Diameter at 10% Volume-weighted distribution [μm] | Diameter at 50% Volume-weighted distribution [μm] | Diameter at 90% Volume-weighted distribution [μm] | Method |
|---|---|---|---|---|---|---|---|---|---|---|
| | Type | Wt % | Type | Wt % | Type | Wt % | | | | |
| 1 | Permalyn 5095 | 1% | Perfume | 1% | [none] | — | 31.8 | 58.2 | 84.7 | Image analysis |
| 2 | Permalyn 5095 | 1.5% | Perfume | 1% | [none] | — | 31.8 | 75.4 | 146.5 | Image analysis |
| 3 | Permalyn 5095 | 0.5% | Perfume | 1% | Surfadone ™ LP-300 | 0.5% | 3 | 7 | 17 | Microscopy |

As shown in Table 3, relatively more plant rosin material tends to result in relatively larger particles; see, e.g., Leg 1 vs. Leg 2. Additionally, it is believed that the presence of an emulsifying agent such as Surfadone™ facilitates the formation of relatively smaller particles.

Example 3. Ratios of Plant Rosin and Benefit Agent

The following rosin/perfume premixes are prepared, as shown in Table 3. The weight percentages are based on weight of the premix composition.

The premixes are provided at levels that provide the same total perfume to a liquid fabric enhancer (LFE) base composition; the total perfume present in the resulting liquid fabric (LFE) compositions is 0.6 wt %. The resulting liquid conditioning product is used to treat a fabric according to the method provided above.

Dry fabric odor (DFO) is assessed using headspace analysis, and the results are provided in Table 3.

TABLE 3

| Premix # | Plant Rosin Material | | Benefit Agent | | DFO Headspace (nM/L) |
|---|---|---|---|---|---|
| | Type | Wt % | Type | Wt % | |
| 1 | Permalyn 5095 | 0% | Perfume | 100% | 0.08 |
| 2 | Permalyn 5095 | 60% | Perfume | 40% | 52 |
| 3 | Permalyn 5095 | 70% | Perfume | 30% | 62 |
| 4 | Permalyn 5095 | 80% | Perfume | 20% | 110 |

As shown in Table 3, perfume in the DFO Headspace (nM/L) increases as the amount of plant rosin material in the premix increases.

Figure 2A:
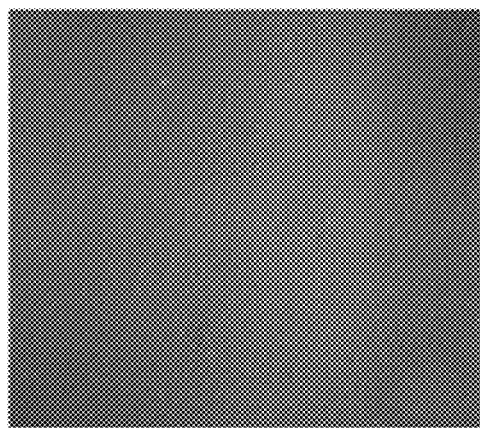
FIG. 2A shows a liquid treatment composition made with Premix #1, as described in Example 3 below.
Figure 2B:
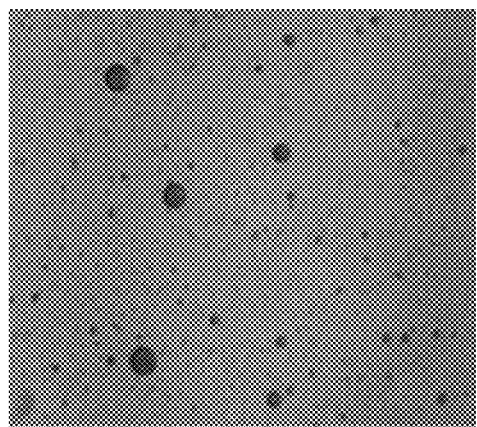
FIG. 2B shows a liquid treatment composition made with Premix #2, as described in Example 3 below.
Figure 2C:
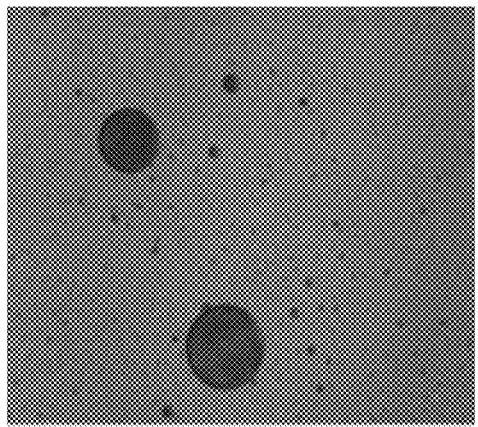
FIG. 2C shows a liquid treatment composition made with Premix #3, as described in Example 3 below.
Figure 2D:
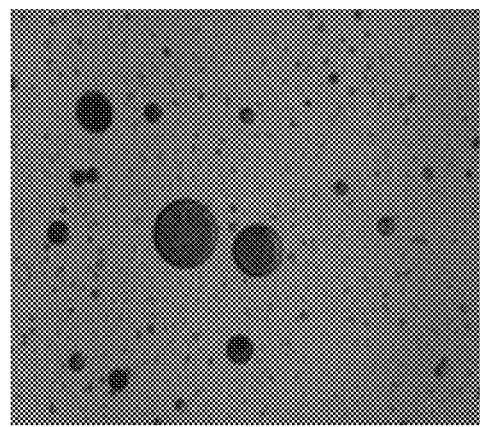
FIG. 2D shows a liquid treatment composition made with Premix #4, as described in Example 3 below.

Additionally, micrographs of the final liquid conditioning products made with Premixes 1, 2, 3, and 4 are obtained, at 10× magnification with polarized transmitted light. As shown in FIG. 2A, particles are not visible in a liquid composition made with Premix 1, which does not include a plant rosin material. As shown in FIGS. 2B-2D, particles are visibly present in the liquid compositions made with Premixes 2 (FIG. 2B), 3 (FIG. 2C), and 4 (FIG. 2D). Furthermore, it appears that the particles are relatively larger in the compositions that include premixes having relatively larger amounts of the plant rosin material; see, e.g., the micrographs of the products made with Premixes 3 (FIG. 2C) and 4 (FIG. 2D).

Example 4. Freshness Benefits

A liquid fabric (LFE) base composition according to Table 4 A, below, is provided.

TABLE 4A

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Structuring agent[2] | 0.2% |
| Water | Balance to 100% |

[1]Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])
[2]FLOSOFT ™ FS 222 (ex SNF Floerger ®)

The following rosin/perfume premixes are prepared, some with an emulsifying agent, as shown in Table 4B. The weight percentages are based on weight of the premix composition.

TABLE 4B

| Premix # | Plant Rosin Material | | Benefit Agent | | Emulsifying Agent | |
|---|---|---|---|---|---|---|
| | Type | Wt % | Type | Wt % | Type | Wt % |
| 1 | Permalyn 5095 | 70% | Perfume | 30% | — | — |
| 2 | Permalyn 5095 | 25% | Perfume | 40% | Soluplus | 35% |
| 3 | Permalyn 5110 | 70% | Perfume | 30% | — | — |
| 4 | Permalyn 5110 | 25% | Perfume | 40% | Soluplus | 35% |
| 5 | Poly-Pale | 25% | Perfume | 40% | Soluplus | 35% |
| 6 | Foral 85 | 70% | Perfume | 30% | — | — |
| 7 | Foral 85 | 25% | Perfume | 40% | Soluplus | 35% |
| 8 | Abalyn D-E | 70% | Perfume | 30% | — | — |
| 9 | Deresinate TX | 70% | Perfume | 30% | — | — |
| 10 | Foralyn E | 70% | Perfume | 30% | — | — |
| 11 | Gum Rosin | 25% | Perfume | 40% | Soluplus | 35% |
| 12 | Gum Rosin | 70% | Perfume | 30% | — | — |
| 13 | Lurefor 125 | 25% | Perfume | 40% | Soluplus | 35% |
| 14 | Foral 105 | 25% | Perfume | 40% | Soluplus | 35% |
| 15 | Staybelite Resin E | 70% | Perfume | 30% | — | — |
| 16 | Zincogral Z | 25% | Perfume | 40% | Soluplus | 35% |

Various liquid fabric conditioning products are made with the premixes in Table 4B and added to the composition of Table 4A. For each leg, a parallel product is made that only adds the perfume (no premix; no plant rosin material) which is used as reference product. Premixes in Table 4B are added in an amount to deliver the same amount of perfume to respect of the reference product (no premix, no plant rosin material). The premixes can be added to the composition of Table 4A while overhead mixing or while mixing with Ultraturrax®.

TABLE 4C

| Leg | Premix used in LFE | Plant Rosin Material | Perfume level (wt %) | Procedure of addition of premix |
|---|---|---|---|---|
| A | 1 | Permalyn 5095 | 1.0% | While Overhead mixing |
| B | 2 | Permalyn 5095 | 1.0% | While Overhead mixing |

TABLE 4C-continued

| Leg | Premix used in LFE | Plant Rosin Material | Perfume level (wt %) | Procedure of addition of premix |
|---|---|---|---|---|
| C | 3 | Permalyn 5110 | 1.0% | While Overhead mixing |
| D | 4 | Permalyn 5110 | 1.0% | While Overhead mixing |
| E | 5 | Poly-Pale | 1.0% | While Overhead mixing |
| F | 6 | Foral 85 | 1.0% | While Overhead mixing |
| G | 7 | Foral 85 | 1.0% | While Overhead mixing |
| H | 8 | Abalyn D-E | 0.6% | While UltraTurrax |
| I | 9 | Deresinate TX | 0.6% | While UltraTurrax |
| J | 10 | Foralyn E | 0.6% | While UltraTurrax |
| K | 11 | Gum Rosin | 0.3% | While Overhead mixing |
| L | 12 | Gum Rosin | 0.3% | While Overhead mixing |
| M | 13 | Lurefor 125 | 0.3% | While Overhead mixing |
| N | 14 | Foral 105 | 1.0% | While Overhead mixing |
| O | 15 | Staybelite Resin E | 0.6% | While UltraTurrax |

The products are used to treat fabrics according to the method provided above, and the dry fabric odor (DFO) for each is measured. The formulation of the LFE composition is reported in Table 4B:

The results are provided in Table 4D below. Additionally, Table 4D shows the "Delta DFO," showing the difference between the DFO scores for the products that include the premixes of Table 4B and the products that only include the perfume. Furthermore, the "DFO Ratio" is the ratio of the two DFO scores in that leg. Relatively higher Delta DFO scores and DFO Ratios indicate that the formulations comprising the premixes are providing freshness benefit compared to perfume-only formulations.

Additionally, a comment on dispersibility is provided for the premixes, based on observations made while trying to disperse the premix into the LFE base composition. Premix 16 was not tested.

TABLE 4D

| Leg | Premix used in LFE | Plant Rosin Material | DFO Headspace (nM/L) (perfume + plant rosin) | DFO Headspace (nM/L) (perfume only) | Delta DFO | DFO Ratio | Dispersibility of Premix (1-5) [2] |
|---|---|---|---|---|---|---|---|
| A | 1 | Permalyn 5095 | 60.2 | 6.12 | +54.08 | 9.8 | 3 |
| B | 2 | Permalyn 5095 | 17.8 | 6.12 | +11.68 | 2.9 | 3 |
| C | 3 | Permalyn 5110 | 149.0 | 4.61 | +144.39 | 32.3 | 4 |
| D | 4 | Permalyn 5110 | 15.9 | 6.12 | +9.78 | 2.6 | 3 |
| E | 5 | Poly-Pale | 8.68 | 6.12 | +2.56 | 1.4 | 2 |
| F | 6 | Foral 85 | 88.54 | 4.61 | +83.93 | 19.2 | 3 |
| G | 7 | Foral 85 | 8 | 6.12 | +1.88 | 1.3 | 2 |
| H | 8 | Abalyn D-E | 2.57 | 0.33 | +2.24 | 7.8 | 1 |
| I | 9 | Deresinate TX | 2.12 | 0.33 | +1.79 | 6.4 | 1 |
| J | 10 | Foralyn E | 44.23 | 0.33 | +43.9 | 134.0 | 4 |
| K | 11 | Gum Rosin | 0.69 | 0.59 | +0.1 | 1.2 | 3 |
| L | 12 | Gum Rosin | 1.58 | 0.59 | +0.99 | 2.7 | 5 |
| M | 13 | Lurefor 125 | 1.57 | 0.59 | +0.98 | 2.7 | 3 |
| N | 14 | Foral 105 | 16.6 | 6.12 | +10.48 | 2.7 | 2 |
| O | 15 | Staybelite Resin E | 2.12 | 0.33 | +1.79 | 6.4 | 1 |

[2] Dispersibility is relative to the ease of dispersing the rosin/perfume (and emulsifying agent, if any) premix in the finished product formulation, where 5 = very difficult to disperse, 3 = average dispersibility, and 1 = good dispersibility.

Figure 3A:
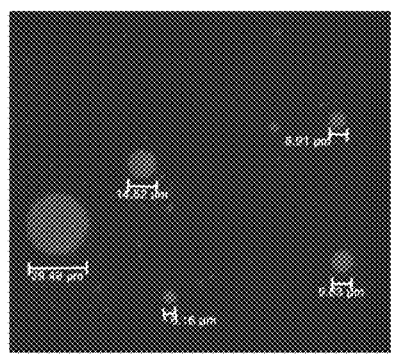
FIG. 3A shows a liquid fabric conditioning product made according to Leg A, as described in Example 4 below.
Figure 3B:
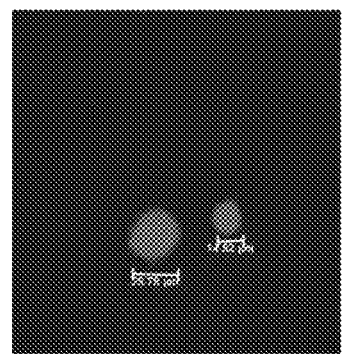
FIG. 3B shows a liquid fabric conditioning product made according to Leg D, as described in Example 4 below.
Figure 3C:
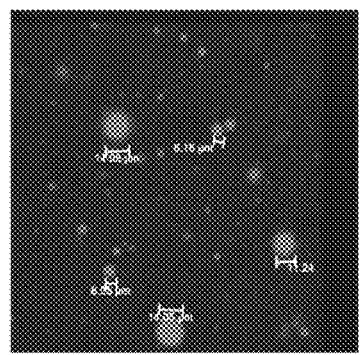
FIG. 3C shows a liquid fabric conditioning product made according to Leg G, as described in Example 4 below.

Additionally, micrographs of some of the liquid fabric conditioning products are provided in FIGS. 3A, 3B, and 3C. The micrographs are taken with fluorescence confocal laser scanning microscopy (CLSM), at a magnification of 63×. The figures show micrographs of samples of the premix-containing products from Leg A (FIG. 3A), Leg D (FIG. 3B), and Leg G (FIG. 3C) at 63×. Particles can be seen in each of the products.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid treatment composition comprising particles and an adjunct ingredient,
   wherein the particles comprise a plant rosin material and one or more benefit agents,
   wherein the one or more benefit agents are encapsulated in the plant rosin material, and/or are partially embedded in the plant rosin material, and
   wherein the liquid treatment composition further comprises an amphiphilic polymer.

2. The liquid treatment composition according to claim 1, wherein the particles are characterized by a volume-weighted median particle size of from about from about 10 microns to about 400 microns.

3. The liquid treatment composition according to claim 1, wherein the plant rosin material and the one or more benefit agents are present in the particles in a weight ratio of from about 5:95 to about 95:5.

4. The liquid treatment composition according to claim 1, wherein the plant rosin material comprises a material selected from the group consisting of gum rosin, wood rosin, tall oil rosin, derivatives thereof, and mixtures thereof.

5. The liquid treatment composition according to claim 1, wherein the plant rosin material is a plant rosin ester.

6. The liquid treatment composition according to claim 1, wherein the plant rosin material is at least partially hydrogenated.

7. The liquid treatment composition according to claim 1, wherein the plant rosin material comprises at least 50%, by weight of the plant rosin material, of an abietic acid, an neoabietic acid, a dehydroabietic acid, a palustric acid, a levopimaric acid, a derivative of an abietic acid, or a mixture thereof.

8. The liquid treatment composition according to claim 1, wherein the plant rosin material is characterized by at least one of the following:
   (a) a softening point of from about 50° C. to about 175° C.;
   (b) an acid number of less than about 175;
   (c) a color grade of from about 1 to about 10, as graded on the Gardner Color standard number.

9. The liquid treatment composition according to claim 1, wherein the one or more benefit agents is selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, antiperspirant actives, emollients, skin sensates, and mixtures thereof.

10. The liquid treatment composition according to claim 1, wherein the one or more benefit agents comprises a fragrance material.

11. The liquid treatment composition according to claim 10, wherein the fragrance material comprises from about 1% to about 40%, by weight of the fragrance material, of Quadrant I perfume raw materials, and/or from about 60% to about 99%, by weight of the fragrance material, of non-Quadrant I perfume raw materials.

12. The liquid treatment composition according to claim 1, wherein the liquid treatment composition is formed by a process comprising adding a premix to a base composition, wherein the premix comprises the plant rosin material and the one or more benefit agents.

13. The liquid treatment composition according to claim 1, wherein the adjunct ingredient comprises a surfactant system, fabric softening agents, or a combination thereof.

14. The liquid treatment composition according to claim 1, wherein the liquid treatment composition comprises at least 8% water, by weight of the liquid treatment composition.

15. The liquid treatment composition according to claim 1, wherein the liquid treatment composition has a viscosity of from 1 to 1500 centipoises (1-1500 mPa*s) at 20 $s^{-1}$ and 21° C.

16. The liquid treatment composition according to claim 1, wherein the liquid treatment composition further comprises a structurant.

17. The liquid treatment composition according to claim 1, wherein the liquid treatment composition is a consumer product composition,
   wherein the consumer product composition is a fabric care composition, a hard surface cleaner composition, a dish care composition, a hair care composition, a body cleansing composition, or a mixture thereof.

18. A method of treating a surface, the method comprising the step of contacting the surface with the liquid treatment composition according to claim 1, optionally in the presence of water.

* * * * *